(12) United States Patent
Chung et al.

(10) Patent No.: US 7,973,084 B2
(45) Date of Patent: *Jul. 5, 2011

(54) MOLECULAR TRANSPORTERS BASED ON ALDITOL OR INOSITOL AND PROCESSES FOR THE PREPARATION THEREOF

(75) Inventors: Sung-Kee Chung, Pohang-si (KR); Woo Sirl Lee, Seoul (KR); Kaustabh Kumar Maiti, Pohang-si (KR)

(73) Assignee: Postech Academy-Industrial Foundation, Kyungsangbuk-do (KR)

( * ) Notice: Subject to any disclaimer, the term of this patent is extended or adjusted under 35 U.S.C. 154(b) by 834 days.

This patent is subject to a terminal disclaimer.

(21) Appl. No.: 11/844,455

(22) Filed: Aug. 24, 2007

(65) Prior Publication Data

US 2008/0039421 A1    Feb. 14, 2008

Related U.S. Application Data

(63) Continuation-in-part of application No. 11/815,339, filed as application No. PCT/KR2005/002040 on Jun. 29, 2005.

(30) Foreign Application Priority Data

Apr. 28, 2005  (KR) .................. 10-2005-0035410
Sep. 7, 2006   (KR) .................. 10-2006-0086106

(51) Int. Cl.
*A01N 31/00* (2006.01)
*A01N 33/18* (2006.01)
*A01N 33/24* (2006.01)
*A61K 31/45* (2006.01)
*A61K 31/04* (2006.01)
*A61B 5/055* (2006.01)

(52) U.S. Cl. ........ 514/738; 514/724; 514/727; 514/740; 424/9.35

(58) Field of Classification Search .................. 514/738, 514/724, 727, 740; 424/9.35
See application file for complete search history.

(56) References Cited

U.S. PATENT DOCUMENTS 6,495,663 B1   12/2002  Rothbard et al.

FOREIGN PATENT DOCUMENTS

| JP | 2002-502388 A | 1/2002 |
|---|---|---|
| JP | 2002-544241 A | 12/2002 |
| WO | WO 7900515 A1 | 8/1979 |
| WO | WO 9404686 A1 | 3/1994 |
| WO | 9419314 A1 | 9/1994 |
| WO | 9854130 A1 | 12/1998 |
| WO | 0069470 A2 | 11/2000 |
| WO | WO 2006/115312 A1 * | 11/2006 |

OTHER PUBLICATIONS

Maiti, K.K., Lee, W.S., Takeuchi, T., Watkins, C., Fretz, M., Kim, D.-C., Futaki, S., Jones, A., Kim, K.-T., Chung, S.-K. (2007) Guanidine-Containing Molecular Transporters: Sorbitol-Based Transporters Show High Intracellular Selectivity toward Mitochondria. Angewandte Chemie, International Edition, vol. 46, p. 5880-5884.*
Maiti, K.K., Jeon, O.-Y., Lee, W.S., Kim, D.-C., Kim, K.-T., Takeuchi, T., Futaki, S., Chung, S.-K. (2006) Design, Synthesis and Membrane-Translocation Studies of Inositol-Based Transporters. Angewandte Chemie, International Edition, vol. 45, p. 2907-2912.*
Paul, A.W., et al., "The Design, Synthesis, and Evaluation of Molecules that Enable or Enhance Cellular Uptake: Peptoid Molecular Transporters," Proc. Natl. Acad. Sci. USA., vol. 97, 13003-13008, 2000.
Pawell, S. et al., "Tat-Medicated Delivery of Heterologous Proteins into Cells," Proc. Natl. Acad. Sci. USA., vol. 91: 664-668 (1994).
Brugidou, J., et al., "The Retro-inverso Form of a Homeobox-Derived Short Peptide is Rapidly Internalized by Cultured Neurons: A New Basis for an Efficient Intracellular Delivery System," Biochem. Biophys. Res. Comm., vol. 214: 685-693 (1995).
30th Anniversary Int'l Symposium, Proceeding of the Chem-Vision in Life Sciences, Aug. 25, 2006.
Wender et al., "Proceedings of the National Academy of Sciences," 2000, vol. 97, No. 24, pp. 13003-13008.

* cited by examiner

*Primary Examiner* — Shaojia Anna Jiang
*Assistant Examiner* — Scarlett Goon
(74) *Attorney, Agent, or Firm* — Sughrue Mion, PLLC

(57) ABSTRACT

The inventive molecular transporter compound shows significantly high permeability through a biological membrane such as plasma membrane, nuclear membrane and blood-brain barrier, and accordingly, it can be effectively used in delivering various biologically active molecules, such as doxorubicin and paclitaxel to target cells.

4 Claims, 2 Drawing Sheets

(2 of 2 Drawing Sheet(s) Filed in Color)

US 7,973,084 B2

MOLECULAR TRANSPORTERS BASED ON ALDITOL OR INOSITOL AND PROCESSES FOR THE PREPARATION THEREOF

This is a Continuation-In-Part of application Ser. No. 11/815,339 filed Aug. 2, 2007, which is a National Stage 371 Application of PCT/KR2005/002040 filed Jun. 29, 2005. The entire disclosure(s) of the prior application(s), application Ser. No. 11/815,339 and PCT/KR2005/002040 are hereby incorporated by reference.

FIELD OF THE INVENTION

The present invention relates to molecular transporters having improved membrane permeability, which are composed of a plurality of guanidine residues and a sugar residue or its analogue, and processes for the preparation thereof.

BACKGROUND OF THE INVENTION

The plasma membrane of a cell separates the cytoplasm of the cell from its outer environment, and it is primarily composed of a phospholipid bilayer and proteins embedded in the bilayer or attached to the surface thereof. Normally the plasma membrane functions as a gatekeeper which controls trafficking of essential substances into and out of the cell. However, the cell plasma membrane also functions as a permeability barrier and blocks the passage of many useful therapeutic agents. Generally, hydrophilic molecules, highly charged molecules and macromolecules such as nucleic acid, or genes meet difficulties in crossing the cell membranes. Therefore, there is a need for a reliable means of transporting drugs and macromolecules into cells.

Heretofore, a number of transporter molecules such as lipids, polymers, and dendrimers have been proposed to be capable of escorting target molecules across biological membranes, but because they are not water soluble or biodegradable, they tend to precipitate in the cell to cause toxicity.

Proteins having a PTD (protein transduction domain) that allows protein permeation through the plasma membrane include HIV-1 Tat peptide, Antennapedia (Antp) homeodomain protein, Herpes virus protein VP22, and Nuclear localization signal (NLS) sequence.

The above-mentioned protein domain seems to facilitate the permeation across biological membranes without the help of any specific transporter or receptor associated with the cell. Further, they contain a high content of basic amino acid residues such as arginine and lysine. For example, the basic region (i.e., 49-57 a.a.) of the Tat protein, which is a necessary transacting transcriptional activator of HIV virus reproduction, has been reported to play a critical role in the process of the protein permeation through the plasma membrane. A number of studies have reported that various oligopeptides having a multiple arginine residues can be used as molecular transporters.

From these studies, it has been found that oligomers having eight to nine arginine residues show the highest permeability and are most effective in enhancing the transportation of molecules attached thereto across a biological membrane, suggesting that the guanidine group of arginine plays a crucial role in the transportation of molecules attached thereto across a biological membrane.

Wender et al. designed peptoid molecular transporters based on the fact that the biological membrane permeability of a peptide largely depends on the number of the guanidine group in the peptide, the length of the linker chain, and the chirality thereof. It was found that an L-arginine nonamer is 20-times more effective in the transportation across a biological membrane than Tat protein (49-57 a.a.), and a D-arginine nonamer was also much more effective in the uptake by Jurkat cells, as was determined using FACS (P. A. Wender, et al., Proc. Natl. Acad. Sci. U.S.A. 97: 13003, 2000). These results suggest that the permeability of peptides having a specific number of guanidine groups is not significantly dependent on by the chirality of the amino acid (U.S. Pat. No. 6,495,663; Korean Patent Laid-Open Publication No. 2001-12809).

However, such polyarginine peptide or related peptoid molecules have the problems of being eliminated by rapid metabolism in the liver and kidney and the tendency that they show in vivo toxicity. Further, a peptide or peptoid having a plurality of guanidine residues can maintain its helical structure only in a basic environment, and this fact suggests that its membrane permeability depends largely on the positively charged guanidinium groups rather then the secondary or tertiary structure thereof.

The present inventors have therefore endeavored to develop molecular transporters prepared by introducing positively charged guanidinium groups to sugar or its analogue having a linear or branched form with a high density of functionality, and have found that such molecular transporters significantly enhance the transportation of various physiologically active molecules attached thereto either covalently or ionically, across a biological membrane.

SUMMARY OF THE INVENTION

Accordingly, it is a primary object of the present invention to provide an alditol- or inositol-based molecular transporter having improved permeability, which are effective in the transportation of a physiologically active molecule across a biological membrane, and a process for the preparation thereof.

It is another object of the present invention to provide a composition for delivering a physiologically active molecule into a cell, comprising the alditol- or inositol-based molecular transporter.

It is a further object of the present invention to provide a method for delivering a physiologically active molecule into a cell, employing the alditol- or inositol-based molecular transporter.

BRIEF DESCRIPTION OF THE DRAWINGS

The patent or application file contains at least one drawing executed in color. Copies of this patent or patent application publication with color drawing(s) will be provided by the Office upon receipt and payment of the necessary fee.

The above and other objects and features of the present invention will become apparent from the following description of the invention, when taken in conjunction with the accompanying drawings, which respectively show.

DETAILED DESCRIPTION OF THE INVENTION

Figure 1:
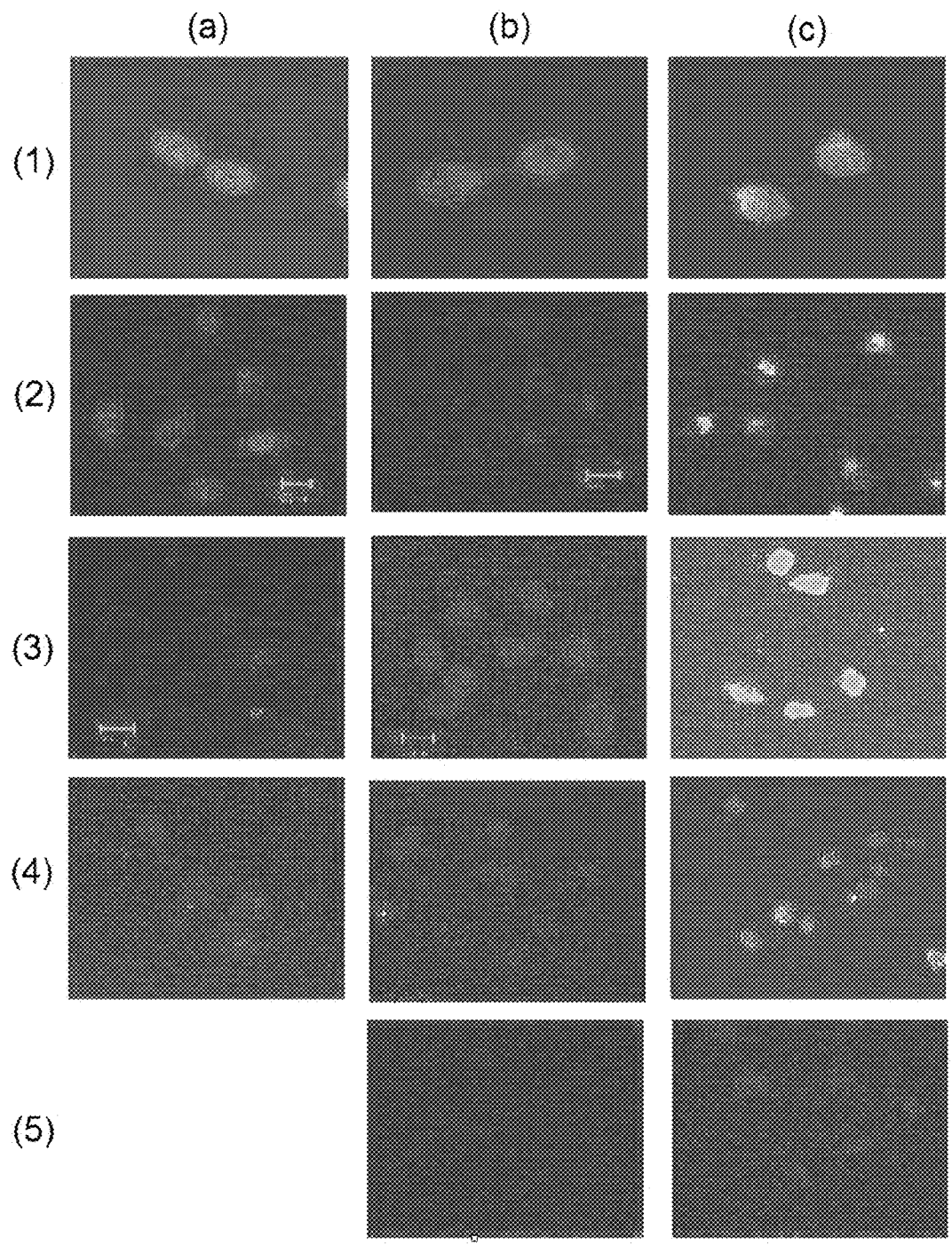
FIG. 1: Results of relative cellular membrane permeabilities of the molecular transporters of the present invention, FITC-conjugated arginine nonamer (Fl-$Arg_9$) and doxorubicin itself, observed by a confocal microscope.

In accordance with one aspect of the present invention, there is provided an alditol- or inositol-based molecular transporter compound of formula 1 or 2, which has a linear or branched form of guanidine groups:

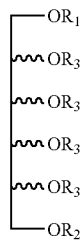

<Formula 1> wherein, $R_1$ and $R_2$ are each independently H, alkyl, arylalkyl, cycloalkyl, heteroalkyl, —$(CH_2)_m NHR'$, —$(CH_2)_l CO_2 R''$, —COR''', —$SO_2 R''''$, a basic amino acid residue, a fluorescent tag, or a physiologically active molecule selected from the group consisting of doxorubicin and paclitaxel, with the proviso that at least one of $R_1$ and $R_2$ is doxorubicin, paclitaxel, —COR''' or a basic amino acid residue;

R', R'', R''' and R'''' are each independently H, alkyl, arylalkyl, cycloalkyl, heteroalkyl or a physiologically active molecule selected from the group consisting of doxorubicin and paclitaxel;

m is an integer in the range of 2 to 5;

l is an integer in the range of 1 to 5; and $R_3$ is

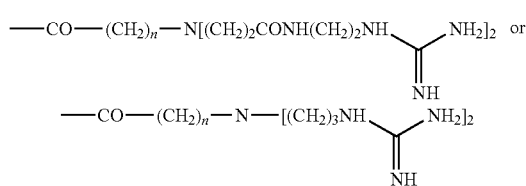

, n being an integer in the range of 1 to 12; or

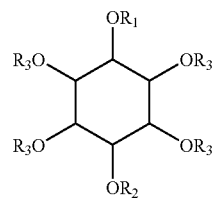

<Formula 2> wherein, $R_1$ and $R_2$ are each independently H, alkyl, arylalkyl, cycloalkyl, heteroalkyl, —$(CH_2)_m NHR'$, —$(CH_2)_l CO_2 R''$, —COR''', —$SO_2 R''''$, a fluorescent material, a diagnostic reagent or a physiologically active molecule;

R', R'', R''' and R'''' are each independently H, alkyl, arylalkyl, cycloalkyl, heteroalkyl or a physiologically active molecule;

m is an integer in the range of 2 to 5;

l is an integer in the range of 1 to 5; and $R_3$ is

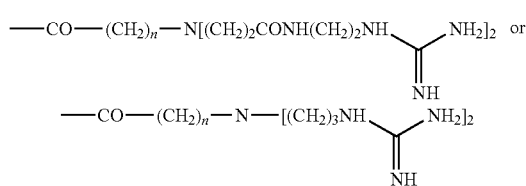

, n being an integer in the range of 1 to 12.

The term "alkyl" refers to a linear or branched saturated hydrocarbon of 1 to 30 carbons, e.g., methyl, ethyl, propyl, isopropyl, n-butyl, tertiary butyl or neopentyl.

The term "aryl" refers to a monocyclic aromatic group or a bicyclic compound having one or more aromatic rings, and the term "arylalkyl" refers to $C_{1-6}$ alkyl having 1 to 3 aryl substituents, e.g., benzyl, trityl and phenylethyl.

The term "cycloalkyl" refers to saturated monocyclic hydrocarbon of 3 to 8 carbons, including but not limited to cyclopropyl, cyclobutyl, cyclopentyl, cyclohexyl and cycloheptyl.

Further, the term "heteroalkyl" refers to alkyl of 1 to 6 carbons having one or more heteroatoms, the heteroatoms being oxygen, sulfur or nitrogen.

Further, the term "basic amino acid" refers to an amino acid having basic moieties, including but not limited to histidine, lysine and arginine.

The compounds of formula 1 according to the present invention is a molecular transporter having eight guanidine groups introduced at the hydroxy terminals of a sugar derivative, which is capable of holding the functional group of a target in its skeleton at a high density, especially when branched chains are introduced therein. The compound of formula 1 includes an alditol derivative and a salt thereof having the skeletal structure of sorbitol, mannitol or galactitol, which is exemplified by a sorbitol derivative of formula 3 or a salt thereof.

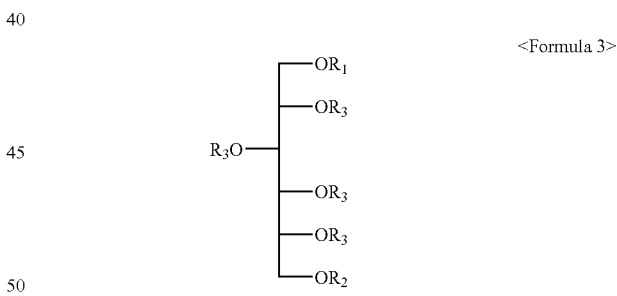

<Formula 3> wherein, $R_1$, $R_2$ and $R_3$ have the same meanings as defined.

Among the compound of the formula 3, preferred are those whose $R_1$ or $R_2$ is

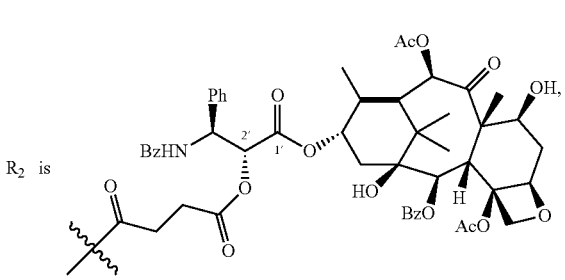

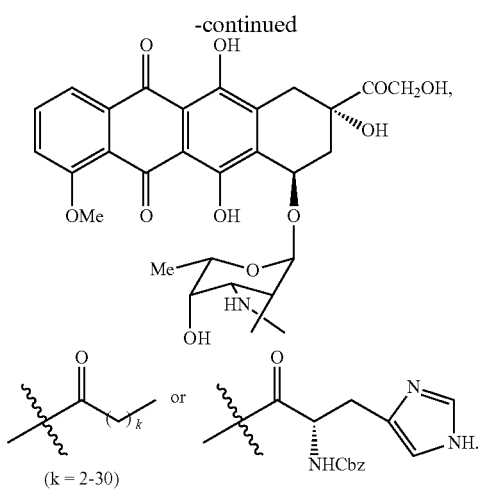

(k = 2-30)

Further, the compound of formula 2 includes an inositol derivative and a salt thereof having the skeletal structure of myo-inositol or scyllo-inositol, which is exemplified by compounds of formulae 4 to 6.

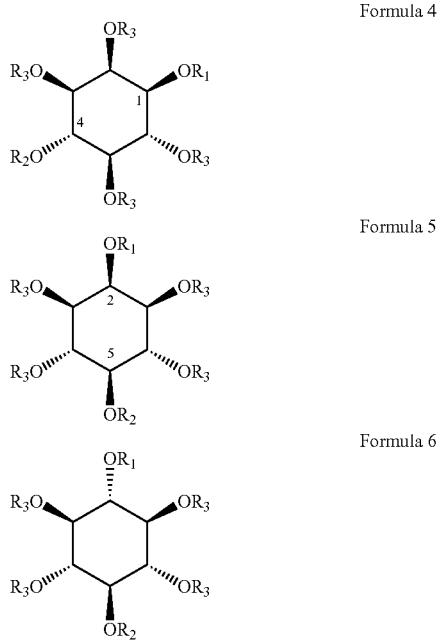

wherein,
$R_1$, $R_2$ and $R_3$ have the same meanings as defined in formula 2.

The molecular transporter compound of formula 1, preferably the compound of formula 3, has functional groups capable of coupling with a physiologically active molecule, and the physiologically active molecule may be doxorubicin or paclitaxel.

As shown in formulae 3 to 6, the molecular transporter compounds of the present invention have either a sorbitol or inositol-based skeleton carrying guanidine groups of a linear or branched chain of variable chain lengths, and therefore, each of them shows a good water-solubility and membrane permeability. Accordingly, the molecular transporter compounds in accordance with the present invention can be attached to a physiologically active molecule such as a drug and diagnostic reagent or a fluorescent tag through either a covalent bond or an ionic bond, which it can be easily transported across a biological membrane, e.g., plasma membrane, nuclear membrane or blood-brain barrier.

Further, the present invention provides a method for preparing the molecular transporter compounds in accordance with the present invention, comprising the steps of:

1) introducing amino acid side chains to the hydroxyl groups of a protected sorbitol or inositol intermediate by acylation to obtain an intermediate compound;

2) introducing protected guanidine groups to the terminal amino groups of the amino acid side chains of the compound obtained in step 1); and 3) removing the protecting groups from the compound obtained in step 2) to provide molecular transporter compounds.

In the inventive method, instead of steps 1) and 2), it is also possible to first prepare the terminal amino acid side chains of the protected guanidine groups, and then to introduce the pre-prepared side chains to the hydroxyl groups of the protected skeletal intermediate by acylation.

More specifically, the method for the preparation of the molecular transporters in accordance with the present invention can be explained depending on the kind of sugar or its analogue skeleton, as follows.

The molecular transporter compounds of formulae 1 and 2, preferably the compounds of formulae 3 to 6, are prepared by the following steps employing the intermediates of formulae 7 to 10 as starting materials, respectively:

1) introducing amino acid side chains to the hydroxyl groups of the protected intermediate by acylation;

2) removing the protecting groups from the terminal amino acid side chains;

3) introducing guanidine groups to the terminal amino groups of the amino acid side chains;

4) removing the protecting groups from the hydroxyl groups of the compound obtained in step 3) and coupling the resulting compound with a physiologically active molecule; and 5) removing the amino protecting groups from the guanidine groups of the compound obtained in step 4).

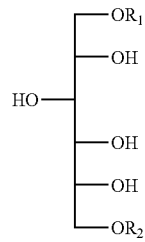

<Formula 7> wherein, $R_1$ and $R_2$ have the same meanings as defined in formula 1.

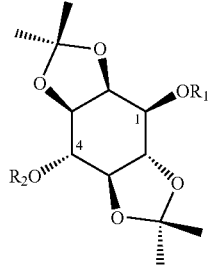

<Formula 8>

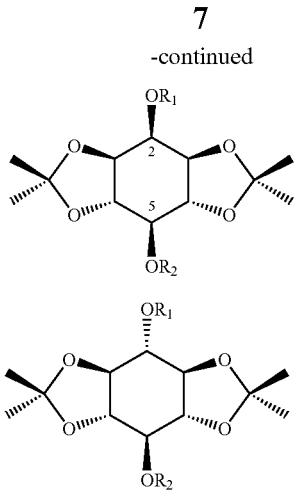

<Formula 9>

<Formula 10> wherein, $R_1$ and $R_2$ have the same meanings as defined in formula 2.

The compound of formula 7, a key intermediate for preparing the compound of formula 3, is an alditol derivative having introduced protecting groups at 1- and 6-OH positions of D-aldohexose such as D-glucose regioselectively, and can be prepared according to the procedure of Scheme 1:

Scheme 1

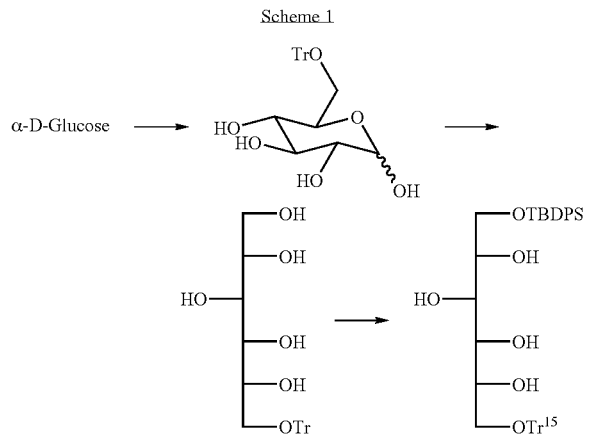

According to Scheme 1 exemplified with D-glucose as a starting material, the intermediate of formula 7 ($R_1$=TBDPS, $R_2$=Tr) can be prepared by selectively introducing a trityl (Tr) protecting group to the 6-OH moiety of D-glucose; performing a reduction reaction, e.g., by using a reducing agent such as sodium borohydride ($NaBH_4$) to obtain D-sorbitol of a linear form; and selectively introducing a t-butyldiphenylsilyl (TBDPS) group to the 1-OH moiety.

Further, the intermediate of formula 8 for preparing the compound of formula 4 can be prepared by synthesizing 2,3:5,6-di-O-isopropylidene-myo-inositol from myo-inositol; and introducing specific protecting groups, e.g., tert-butyldimethylsilyl (TBDMS) or benzyl (Bn) protecting group to the 1-OH or 4-OH group thereof regioselectively.

The intermediate of formula 9 for preparing the compound of formula 5 can be prepared by synthesizing 1,6:3,4-di-O-isopropylidene-myo-inositol from myo-inositol; and introducing specific protecting groups, e.g., p-methoxybenzyl (PMB) or benzyl (Bn) protecting group, to the 2-OH or 5-OH moiety thereof regioselectively.

Further, the intermediate of formula 10 for preparing the compound of formula 6 can be prepared by inverting the stereochemistry of the 2-OH group of myo-inositol through Mitsunobu reaction; synthesizing 1, 6:2,4-di-O-isopropylene-scyllo-inositol therefrom; and introducing different protecting groups, e.g., PMB, benzoyl (Bz) or Bn protecting group, to the 2-OH or 5-OH moiety thereof regioselectively.

In step 1), the amino acid side chains of various lengths are introduced to the protected intermediate by acylation as described above. The intermediates of formulae 8 to 10, except the intermediate of formula 7, are subjected to deprotection of the acetonide protecting groups before the acylation reaction. The acylation reaction is carried out by reacting each intermediate with the amino acid having variable chain lengths with the protected amino groups in the form of carbobenzyloxy (Cbz) groups, in the presence of a condensing agent such as dicyclohexylcarbodiimide and 1-[3-(dimethylamino)propyl]-ethylcarbodiimide hydrochloride. The amino acid having variable chain lengths employed in the present invention can be obtained from commercially available ω (omega)-amino acid, and N,N-di-aminopropyl aminocaproic acid derivatives having terminal amino groups protected with appropriate protecting groups is preferable.

The above acylation reaction may be conducted using the amino acid having variable chain lengths in an amount ranging from 1.5 to 2.5 equivalents based on each functionality of the intermediate at a temperature ranging from 25 to 40° C. for 16 to 72 hrs.

In step 2), the amino protecting groups are removed from the terminal amino groups of the side chains. The deprotection may be performed by adding a catalyst such as palladium (Pd), nickel and platinum to the compound obtained in step 1), stirring the mixture under a hydrogen atmosphere and filtering.

In step 3), the deprotected amino groups of the compound obtained in step 2) are converted into guanidine groups by allowing the compound to react with N,N'-di-Boc-N"-triflylguanidine or N,N'-di-Boc-S-methylisothiourea in the presence of a base in an organic solvent (T. T. Baker, et al., *J. Org. Chem.* 65: 9054, 2000; A. E. Miller and J. J. Bischoff, *Synthesis* 777, 1986). Alternately, it is possible that the guanidine groups are introduced to the terminal amine resides of the side chains in advance, and then, the pre-prepared side chains having the guanidine groups are directly introduced to the skeletal intermediate by acylation. Exemplary organic solvents that may be used in the above step are dichloromethane, N,N-dimethylformamide, chloroform, ethyl acetate, 1,4-dioxane, and the like, and the base may be triethylamine. The above reaction may be carried out at a temperature ranging from 25 to 40° C. for 16 to 72 hrs.

In step 4), the protecting groups are removed from the compound obtained in step 3), and the exposed hydroxyl groups may be used in coupling with a physiologically active molecule or its derivative. It is also possible to introduce a fluorescent tag such as dansyl (5-dimethylamino-1-naphthalene sulfonyl), FITC (Fluorescein) and Rhodamine to the compound by eliminating one of the protecting groups selectively from the compound having the guanidine groups, and then attaching the fluorescent marker.

Finally, the protecting groups are eliminated from the guanidine groups of the compound obtained in step 4), to obtain the inventive molecular transporter compounds of formulae 3 to 6.

Scheme 2 illustrates the procedure for preparing the molecular transporter of formula 3 from the intermediate of formula 7.

Scheme 2

Further, Schemes 3 and 4 respectively illustrate the procedures for preparing the molecular transporters of formulae 4 and 6 from the intermediates of formulae 8 and 10.
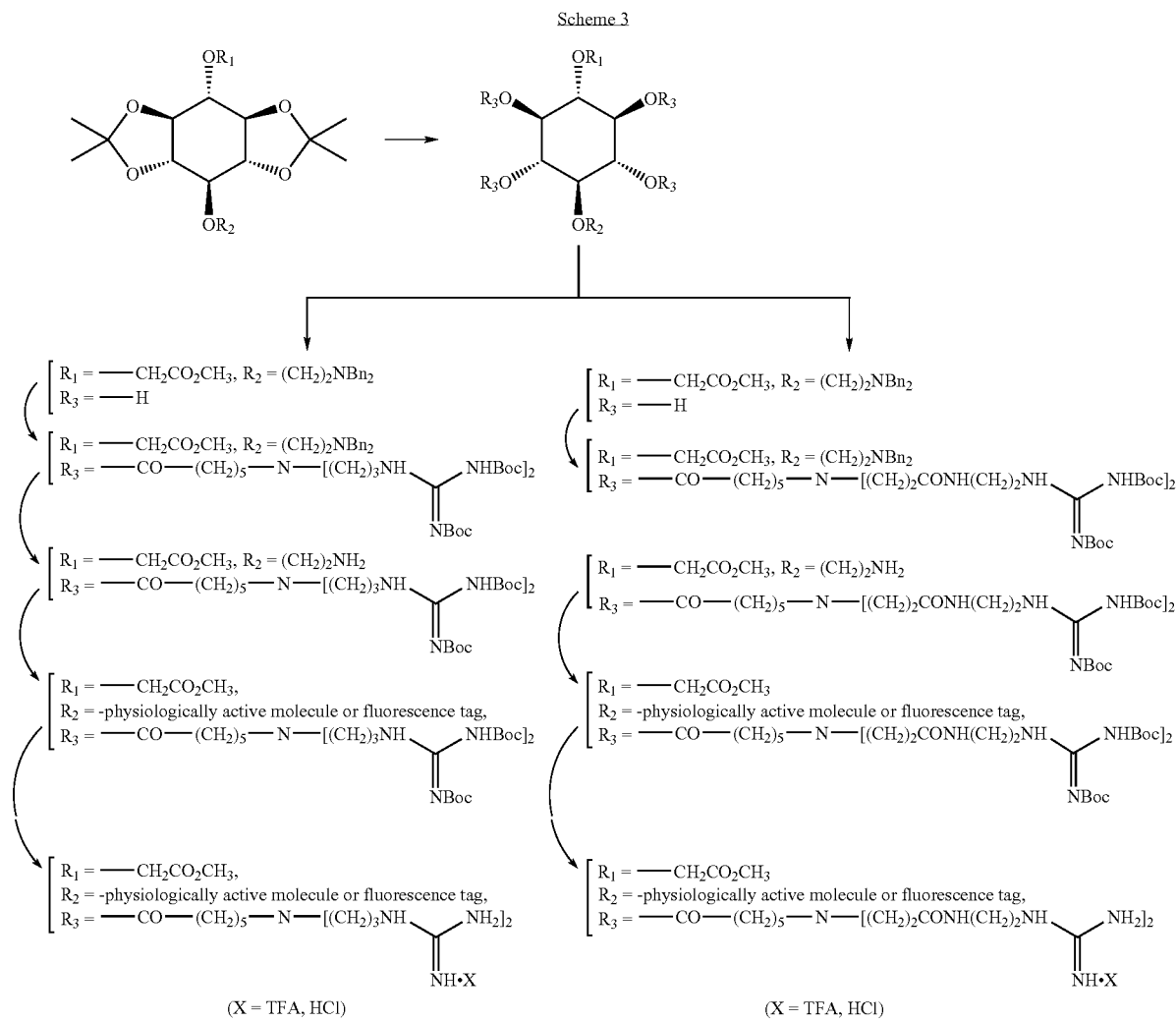
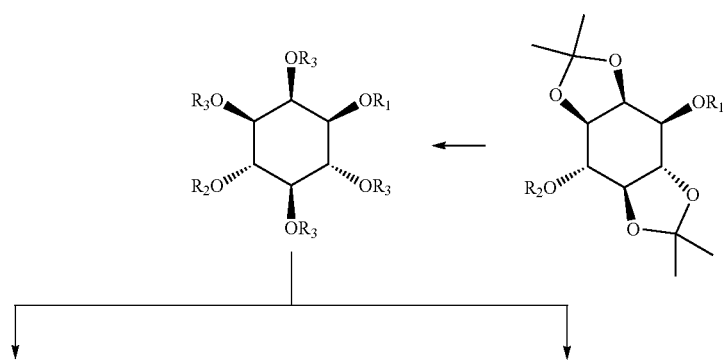

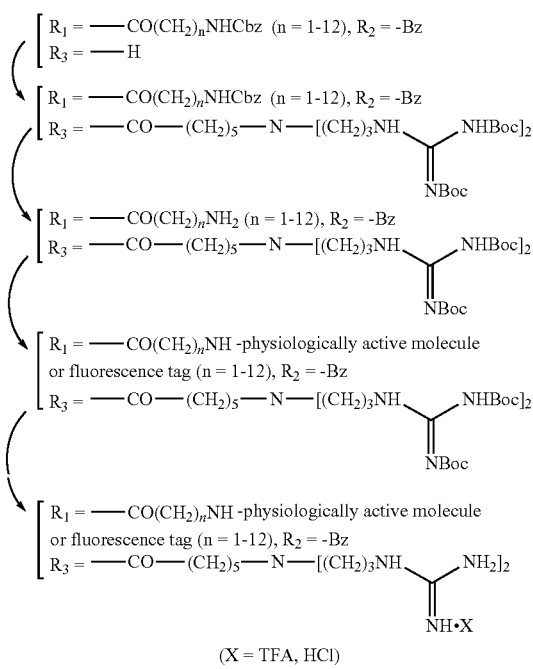

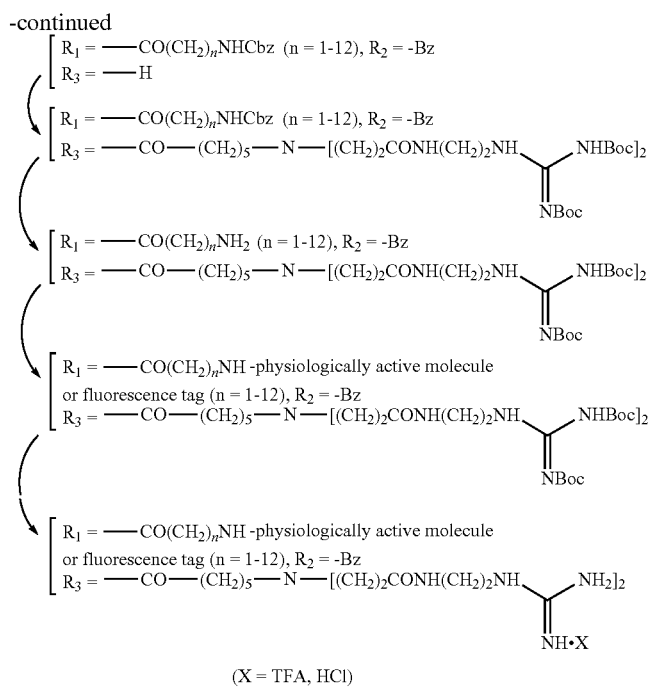

The molecular transporter compound in accordance with the present invention is an alditol- or inositol-based derivative having 8 guanidine groups, and it may be conjugated with a biologically active molecule through a covalent bond or an ionic bond. The conjugate thus formed shows a significantly enhanced uptake by target cells, indicating that the conjugate successfully passed through biological barriers such as a plasma membrane, nuclear membrane and blood-brain barrier.

Accordingly, the molecular transporter compounds of the present invention may be advantageously used in delivering peptides and nucleic acids as well as various therapeutic molecules and diagnostic reagents into cells.

Therefore, the present invention provides a composition for delivering a physiologically active molecule into cells across the biological membrane, comprising one of the molecular transporter compounds of formulae 1 and 2. Further, the present invention provides a method for delivering a physiologically active molecule into a cell across a biological membrane, employing one of the molecular transporter compounds of formulae 1 and 2. Representative examples of the physiologically active molecule are doxorubicin and paclitaxel.

The molecular transporter compounds of formulae 1 and 2 can deliver a biologically active molecule into cells by way of forming complex through an ionic bond, or by forming a conjugate with a biologically active molecule through a covalent bond.

The molecular transporters conjugated with fatty acid, in particular, can deliver DNA/RNA into cells or the nucleus thereof by way of forming an ionic complex with DNA/RNA. Further, the molecular transporters conjugated with fatty acid can be used for the surface modification of liposome so as to effectively deliver a nucleic acid capsulated in liposome into cells/nucleus across the cell and nuclear membranes. In other words, the molecular transporters conjugated with fatty acid can be advantageously used in gene delivery as a condensing agent of nucleic acid or a surface modifying agent of liposome (S. Futaki, et al., *Bioconju. Chem.*, 12, 1005, 2001; and K. Kogure, et al., *J. Control. Release*, 98, 317, 2004).

The following Examples are intended to further illustrate the present invention without limiting its scope.

PREPARATION EXAMPLE 1

Preparation of Sorbitol having Protecting Groups

<1-1> Introduction of Trityl Protecting Group to α-D Glucose

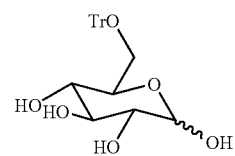

α-D-Glucose (10 g, 55.5 mmol) was dissolved in 120 ml of dry pyridine, and triethylamine (38.7 ml, 277.5 mmol) was added thereto. Tritylchloride (18.3 g, 65.5 mmol) was added dropwise to the mixture, and the mixture was stirred for a day. After the reaction was completed, the reaction mixture was diluted with dichloromethane ($CH_2Cl_2$, 250 ml) and washed with saturated $NaHCO_3$ (100 ml). The organic layer thus obtained was dried over $Na_2SO_4$, concentrated under a reduced pressure, and purified by column chromatography (ethyl acetate:n-hexane=2:3 to 1:1 to 3:2), to obtain the title compound as a light brown solid (16.87 g).

$^1$H-NMR ($CD_3OD$): δ 3.25-3.38(m, 4H), 3.59(t, J=9.2 Hz, 1H), 3.94(m, 1H), 5.13(d, J=3.7 Hz, 2H), 7.11-7.30(m, 9H), 7.42(d, J=9.4 Hz, 6H)

MS (FAB) m/z 445.22($M^+$+Na)

<1-2> Preparation of Sorbitol from the Protected α-D-glucose

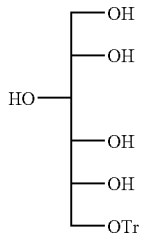

The compound obtained in Preparation Example <1-1> (10 g, 23.66 mmol) was dissolved in methanol (200 ml), sodium borohydride (NaBH$_4$) (2.18 g, 59.18 mmol) was added portionwise thereto, and then, the mixture was stirred at room temperature for 7 hrs. The reaction mixture was concentrated under a reduced pressure, and crystallized from a mixture of water and methanol, to obtain the title compound as a white solid (6.68 g).

$^1$H-NMR (CD$_3$OD): δ 3.25-3.33(m, 4H), 3.47-3.51(m, 2H), 3.85-3.87(m, 2H), 7.14-7.26(m, 9H), 7.42(d, J=8.8 Hz, 6H)

MS (FAB) m/z 447.29(M$^+$+Na)

<1-3> Introduction of t-butyldiphenylsilyl Protecting Group

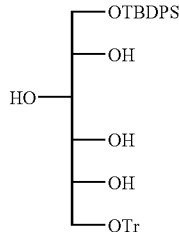

The compound obtained in Preparation Example <1-2> (5 g, 11.77 mmol), triethylamine (4.9 ml, 35.33 mmol), and (4-dimethylamino-pyridine (287.8 mg, 0.235 mmol) were dissolved in N,N-dimethylformamide (50 ml). tert-Butyl-chlorodiphenylsilane (6.12 ml, 23.55 mmol) was added dropwise to the above mixture over a period of an hour, and the resulting mixture was stirred for a day at room temperature. After the reaction was completed, the reaction solution was diluted with ethyl acetate (200 ml) and washed successively with water (50 ml) and saturated NaCl (25 ml). The aqueous layer thus obtained was re-extracted twice with ethyl acetate (50 ml), the combined organic layer was dried over Na$_2$SO$_4$, concentrated under a reduced pressure, and subjected to column chromatography (ethyl acetate:n-hexane=1:1 to 3:2), to obtain the title compound as a white foamy solid (5.5 g).

$^1$H-NMR (CDCl$_3$): δ 1.06(s, 9H), 2.72(brs, 1H), 3.01(brs, 1H), 3.21(brs, 1H), 3.35(d, J=5.5 Hz, 2H), 3.73-3.83(m, 6H), 7.22-7.65(m, 25H)

MS (FAB) m/z 686.24(M$^+$+Na)

PREPARATION EXAMPLE 2

Preparation of Aminocaproic Acid Derivative having Carbobenzoxy Protecting Groups (I)

<2-1> Preparation of N-di-cyanoethylated 6-aminocaproic acid

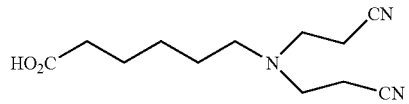

An excess amount of acrylonitrile (94.1 ml, 1.43 mol) and glacial acetic acid (21.8 ml, 0.381 mol) were added dropwise to 6-aminocaproic acid (2.5 g, 0.019 mol), and the mixture was refluxed for 30 hrs. The residual acrylonitrile left over from the reaction was removed by evaporating under a reduced pressure, and acetic acid was removed by repeated cycles of adding toluene and evaporating under a reduced pressure. The reaction mixture was diluted with 200 ml of ethyl acetate and washed with water several times. The organic layer thus obtained was dried over Na$_2$SO$_4$, concentrated under a reduced pressure, and purified by column chromatography (ethyl acetate:n-hexane=4:1), to obtain the title compound as a sticky brown syrup (3.5 g).

$^1$H-NMR (CDCl$_3$): δ 1.35-1.49(m, 4H), 1.65(t, J=7.5 Hz, 2H), 2.36(t, J=7.3 Hz, 2H), 2.46-2.84(m, 6H), 2.86(t, J=6.7 Hz, 4H), 10.35(brs, 1H)

MS (FAB) m/z 238.08(M$^+$+H)

<2-2> Conversion of Cyano Groups into Amino Groups

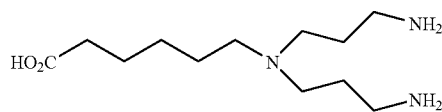

The compound obtained in Preparation Example <2-1> (2.2 g, 1.05 mmol) was dissolved in 75 ml of 95% ethanol, 1 M sodium hydroxide (15 ml) and Raney Nikel catalyst (4 g) were added thereto, and then, the mixture was allowed to react for 24 hrs under hydrogen atmosphere (50 psi). After the reaction was completed, the mixture was filtered through celite to eliminate the catalyst, and washed with 95% ethanol. The filtrate thus obtained was concentrated under a reduced pressure, to obtain the title compound as a sticky white solid (2.25 g).

$^1$H-NMR (CD$_3$OD): δ 1.31-1.68(m, 6H), 1.89(m, 4H), 2.22(t, J=7.2 Hz, 2H), 2.71-2.76(m, 6H), 2.98(t, J=7.5 Hz, 4H)

MS (FAB) m/z 246.15(M$^+$+H)

<2-3> Protection of Amino Groups with Carbobenzoxy Group (Cbz)

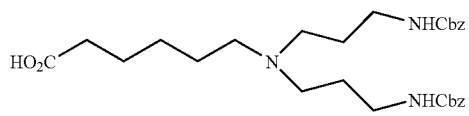

The compound obtained in Preparation Example <2-2> (1.1 g, 6.11 mmol) was dissolved in 20 ml of a 1,4-dioxane: water (2:1) mixture and sodium bicarbonate (2.56 g, 30.57 mmol) was added thereto, followed by slow addition of carbobenzoxychloride (Cbz-Cl)(2.7 ml, 18.34 mmol) to the mixture at 0° C. over 30 mins. After stirring at room temperature for 15 hrs, the reaction mixture was concentrated and diluted with 20 ml of water. 10% HCl was added thereto dropwise until the pH of the mixture became 2, and then, extracted with ethyl acetate. The organic layer thus obtained was dried over Na$_2$SO$_4$, concentrated under a reduced pressure, and purified by column chromatography (dichloromethane:methanol=9:1), to obtain the title compound as a white foamy solid (1.4 g).

$^1$H-NMR (CDCl$_3$): δ 1.33-1.61(m, 6H), 1.94(brs, 4H), 2.27(t, J=6.8 Hz, 2H), 2.93(brs, 6H), 3.20-3.22(m, 4H), 5.01(s, 4H), 5.65(brs, 2H), 7.31(brs, 10H)

MS (FAB) m/z 514.21(M$^+$+H)

<2-4> Conversion of Amino Groups into N,N'-di-Boc-guanidine Group

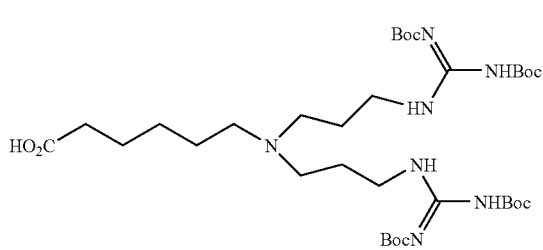

The compound obtained in Preparation Example <2-3> (2 g, 8.15 mmol) was dissolved in 35 ml of a mixture of dioxane and water (5:1), and pH of the reaction mixture was adjusted to 7 by adding 1N HCl. Triethylamine (9.12 ml, 64.89 mmol) and N,N'-di-Boc-N"-triflylguanidine (9.56 g, 24.42 mmol) were added thereto, followed by stirring the mixture at room temperature for 3 days. After the reaction was completed, the reaction mixture was diluted with 150 ml of ethylacetate and successively washed several times with a saturated NaCl solution and water. The organic layer thus obtained was dried over $Na_2SO_4$, concentrated under a reduced pressure, and purified by column chromatography (dichloromethane:methanol=9:1), to obtain the title compound as a white foamy solid (3.86 g).
$^1$H-NMR (CDCl$_3$): δ 1.41-1.49(m, 42H), 1.61-1.70(m, 4H), 2.27-2.31(m, 2H), 2.38-2.49(m, 6H), 3.42-3.49(m, 4H), 8.45(brs, 2H), 11.45(brs, 2H)
MS (FAB) m/z 730.90(M$^+$+H)

PREPARATION EXAMPLE 3

Preparation of aminocaproic acid derivative having Carbobenzoxy Protecting Groups II <3-1> Preparation of N-di-methylacrylated 6-aminocaproic acid

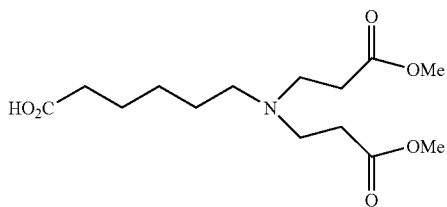

An excess amount of methyl acrylate (77.3 ml, 0.857 mol) and glacial acetic acid (13.1 ml, 0.228 mol) were added dropwise to 6-aminocaproic acid (1.5 g, 0.0114 mol), and the mixture was refluxed for 30 hrs. The remaining methyl acrylate and acetic acid after the reaction were removed by evaporating with added toluene under a reduced pressure. The reaction mixture was diluted with 200 ml of ethyl acetate and washed several times with water. The organic layer thus obtained was dried over $Na_2SO_4$, concentrated under a reduced pressure, and purified by column chromatography (ethyl acetate:n-hexane=4:1), to obtain the tile compound as a viscous brownish syrup (1.85 g).
$^1$H-NMR (CDCl$_3$): δ 1.30-1.62(m, 6H), 2.30(t, J=7.4 Hz, 2H), 2.50(t, J=6.8 Hz, 6H), 2.80-2.86(m, 4H), 3.66(s, 6H)
MS (FAB) m/z 304.18(M$^+$+H)

<3-2> Reaction of Ethylenediamine with the Ester

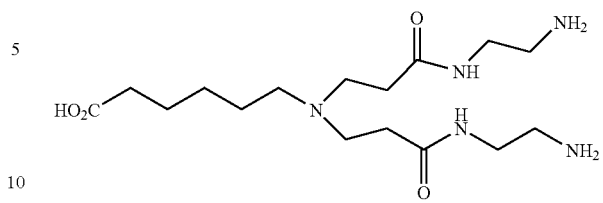

The compound obtained in Preparation Example <3-1> (1.2 g, 3.95 mmol) and ethylenediamine (16 ml, 237.3 mmol) were dissolved in methanol (20 ml) and stirred at room temperature for 72 hrs. The excess amount of ethylenediamine was eliminated by evaporating under a reduced pressure to obtain the title compound as a light brownish syrup (1.4 g).
$^1$H-NMR (CD$_3$OD): δ 1.26-1.64(m, 6H), 2.16-2.22(m, 2H), 2.27-2.56(m, 6H), 2.71-2.88(m, 8H), 3.29-3.31(m, 4H)
MS (FAB) m/z 382.19(M$^+$+Na)

<3-3> Protection of Amino Groups with Carbobenzoxy Group (Cbz)

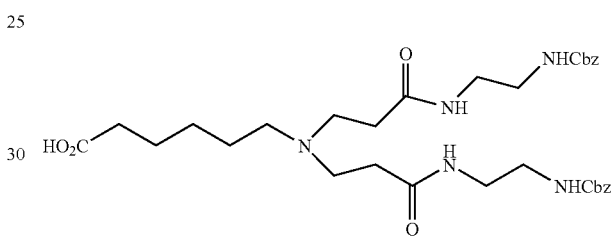

The compound obtained in Preparation Example <3-2> (930 mg, 2.58 mmol) was dissolved in 20 ml of 1,4-dioxane and water mixture (2.5:1), and sodium bicarbonate (1.52 g, 18.11 mmol) was added thereto, followed by slowly adding dropwise 1.4 ml of carbobenzoxychloride (10.34 mmol) to the mixture at 0° C. over a period of 30 min. After stirring at room temperature for 15 hrs, the reaction mixture was concentrated, diluted with 20 ml of water, and 10% HCl was added dropwise to adjust the pH to 2, and then, extracted with ethyl acetate. The organic layer thus obtained was dried over $Na_2SO_4$, concentrated under a reduced pressure, and purified by column chromatography (dichloromethane:methanol=9:1), to obtain the title compound as a white solid (1.2 g).
$^1$H-NMR (CD$_3$OD): δ 1.23-1.71(m, 6H), 2.13(t, J=6.8 Hz, 2H), 2.30-2.48(m, 6H), 2.69(brs, 4H), 3.21-3.26(m, 8H), 5.04 (s, 4H), 7.31-7.32(m, 10H)
MS (FAB) m/z 650.19(M$^+$+Na)

<3-4> Conversion of Amino Groups into N,N'-di-Boc-guanidine Group

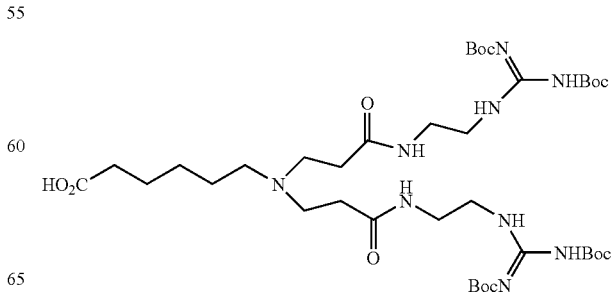

The compound obtained in Preparation Example <3-2> (500 mg, 1.39 mmol) was dissolved in 6 ml of N,N-dimethylformamide, and triethylamine (0.7 ml, 4.86 mmol) and N,N'-di-Boc-N''-triflylguanidine (1.36 g, 3.47 mmol) were added thereto, followed by stirring the mixture at room temperature for 3 days. After the reaction was completed, the reaction mixture was diluted with 100 ml of dichloromethane and successively washed several times with brine and water. The organic layer thus obtained was dried over $Na_2SO_4$, concentrated under a reduced pressure, and purified by column chromatography (dichloromethane:methanol=9:1), to obtain the title compound as a white foamy solid (800 mg).

$^1$H-NMR (CDCl$_3$): δ 1.45-1.66(m, 42H), 2.41-2.44(m, 6H), 2.84(brs, 4H), 3.40-3.54(m, 10H), 8.18(brs, 2H), 8.64 (brs, 2H), 11.44(brs, 2H)

MS (FAB) m/z 844.33(M$^+$+H)

PREPARATION EXAMPLE 4

Preparation of 6-aminocaproic acid Derivative Having N-carbobenzoxy Protecting Groups

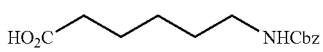

The compound obtained in Preparation Example <3-2> (10 g, 76.23 mmol) was dissolved in 50 ml of a mixture of 1,4-dioxane and water (3:2), sodium bicarbonate (25 g, 297.81 mmol) was added thereto, and carboxybenzoxy chloride (13.4 ml, 95.2 mmol) were added dropwise thereto for 30 min. The mixture was stirred at room temperature for 12 hrs, concentrated under a reduced pressure, 20 ml of water was added thereto, and pH of the reaction mixture was adjusted to 2 by adding 10% HCl, followed by extracting the resulting mixture with ethyl acetate. The organic layer thus obtained was dried over $Na_2SO_4$, concentrated under a reduced pressure, and purified by a column chromatography (dichloromethane:methanol=9:1), to obtain the title compound as a white solid (15 g).

$^1$H-NMR (CDCl$_3$): δ 1.33-1.64(m, 6H), 2.32-2.36(m, 2H), 3.16-3.20(m, 2H), 4.86(brs, 1H), 5.09(s, 2H), 7.25-7.36(m, 5H, aromatic)

MS (FAB) m/z 266.10(M$^+$+H)

PREPARATION EXAMPLE 5

Preparation of Paclitaxel Derivative

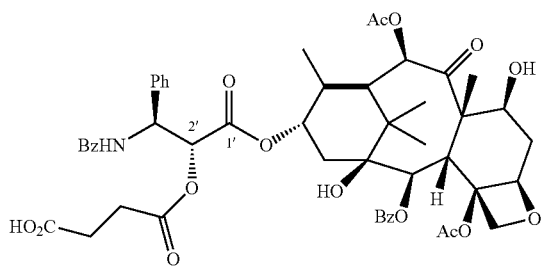

Paclitaxel (100 mg, 0.171 mmol; Waco Pure Chem. Industries, Ltd.) was dissolved in 4 ml of dichloromethane, succinic anhydride (15.2 mg, 0.1522 mmol) and pyridine (catalytic amount, 50 μl) were added thereto, and the mixture was stirred at room temperature for 3 days. After the reaction was completed, the reaction mixture was diluted with 30 ml of dichloromethane and successively washed several times with brine and water. The organic layer thus obtained was dried over $Na_2SO_4$, concentrated under a reduced pressure, and purified by column chromatography (dichloromethane: methanol=10:1), to obtain the title compound as a white solid (82 mg).

$^1$H-NMR (CDCl$_3$): δ 1.12(s, 3H), 1.22(s, 3H), 1.66(s, 3H), 1.90(brs., 5H), 2.03(s, 3H), 2.19(brs., 4H), 2.36-2.60(m, 9H), 3.79(d, J=7.0 Hz, 1H), 4.18(d, J=8.4 Hz, 1H), 4.28(d, J=8.2 Hz, 1H), 4.42(dd, J 1=12.4 Hz, J 2=6.8 Hz, 1H), 4.96(d, J=8.6 Hz, 1H), 5.50(d, J=3.1 Hz, 1H), 5.68(d, J=6.9 Hz, 1H), 5.98 (dd, J 1=12.4 Hz, J 2=3 Hz, 1H), 6.24(t, J=9.1 Hz, 1H), 6.29(s, 1H), 7.20(d, J=9.2 Hz, 1H), 7.30-7.40(m, 7H), 7.43-7.49(m, 3H), 7.59-7.62(m, 1H), 7.74(d, J=7.2 Hz, 2H), 8.12(d, J=7.2 Hz, 2H)

(Y. Tatiana, et al., *J. Am. Chem. Soc. U.S.A.* 127: 12508, 2005)

PREPARATION EXAMPLE 6

Preparation of an Intermediate of Alditol derivative having Eight Guanidine Groups I <6-1> Introduction of Side Chains to Sorbitol by Acylation

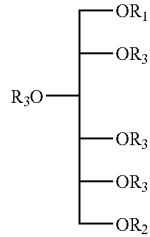

$\left[ \begin{array}{l} R_1 = \text{-TBDPS}, R_2 = \text{-Tr}, \\ R_3 = \text{—CO—}(CH_2)_5\text{—N—}[(CH_2)_3\text{NH-Cbz}]_2 \end{array} \right.$ The sorbitol compound with the 1,6-OH groups protected as obtained in Preparation Example 1 (100 mg, 0.15 mmol), the compound obtained in Preparation Example 2 (757.5 mg, 1.2 mmol) and 4-dimethylamino pyridine (27.6 mg, 0.226 mmol) were dissolved in 5 ml of N,N-dimethylformamide, and 1-[3-(dimethylamino)propyl]-ethylcarbodiimide hydrochloride (231.3 mg, 1.2 mmol) was added thereto, followed by stirring the mixture at room temperature for a day. After the reaction was completed, the reaction mixture was extracted with 50 ml of dichloromethane and the extract was successively washed several times with saturated $NaHCO_3$ solution (30 ml) and water, dried over $Na_2SO_4$, concentrated under a reduced pressure, and purified by column chromatography (dichloromethane:methanol=9:1), to obtain the title compound having introduced four side chains at its skeleton as a white foamy solid (263 mg).

$^1$H-NMR (CDCl$_3$): δ 1.01(s, 9H), 1.17-1.51(m, 40H), 1.86-2.32(m, 32H), 3.31(brs, 16H), 3.60-3.88(m, 2H), 3.93-4.12(m, 2H), 4.79-4.92(m, 2H), 4.98(s, 16H), 5.59(brs, 8H), 5.61-5.88(m, 2H), 7.13-7.59(m, 65H)

MS (MALDI-TOF) m/z 2668.40(M$^+$+Na)

<6-2> Removal of Carbobenzoxy Groups from Terminal Amino Residues of the Side Chains

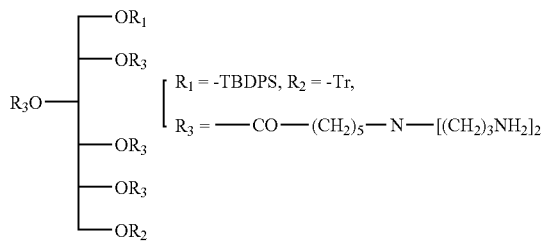

The compound obtained in Example <6-1> (150 mg, 0.056 mmol) was dissolved in 4 ml of methanol and 100 mg of Pd/C was added thereto. The mixture was stirred at room temperature for 15 hrs under $H_2$ atmosphere (50 psi), and filtered through celite to remove the Pd/C catalyst. The filtrate thus obtained was concentrated under a reduced pressure to obtain the title compound as a sticky white solid (87 mg).

$^1$H-NMR (CD$_3$OD): δ 1.02(s, 9H), 1.16-1.82(m, 24H), 2.07-2.38(m, 24H), 3.03-3.28(m, 40H), 3.56-3.80(m, 2H), 3.91-4.13(m, 2H), 4.87-5.13(m, 2H, merged with CD$_3$OD peak), 5.88(dd, J=14.2 Hz, 1.9 Hz, 2H), 7.24-7.68(m, 25H)

MS (MALDI-TOF) m/z 1593.89(M$^+$+Na)

<6-3> Conversion of the Amino Groups into N,N'-di-Boc-guanidine Groups

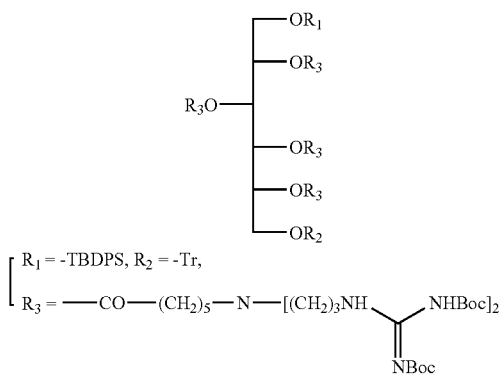

The compound obtained in Example <6-2> (75 mg, 0.0047 mmol) was dissolved in 6 ml of N,N-dimethylformamide, and triethylamine (0.24 ml, 0.166 mmol) and N,N'-di-Boc-N''-triflylguanidine (410 mg, 0.105 mmol) were added thereto, followed by stirring the mixture at room temperature for 2 days. After the reaction was completed, the reaction mixture was diluted with 60 ml of dichloromethane and successively washed with brine and water several times. The organic layer thus obtained was dried over Na$_2$SO$_4$, concentrated under a reduced pressure, and purified by column chromatography (dichloromethane:methanol=10:1), to obtain the title compound having introduced eight guanidine groups as a white foamy solid (104 mg).

$^1$H-NMR (CDCl$_3$): δ 1.03(s, 9H), 1.18-1.54(m, 168H), 2.28-2.64(m, 24H), 2.78-3.28(m, 24H), 3.59(brs, 16H), 3.89-4.21(m, 4H), 4.82(brs, 1H), 5.11(brs, 1H), 5.63(brs, 1H), 5.89(brs, 1H), 7.26-7.67(m, 25H), 8.39(brs, 8H), 11.35(brs, 8H)

MS (MALDI-TOF) m/z 3533.34(M$^+$+Na)

PREPARATION EXAMPLE 7

Preparation of an Intermediate of Alditol Derivative having Eight Guanidine Groups II

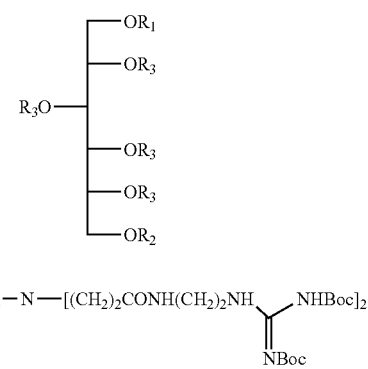

The sorbitol compound with 1,6-OH positions protected as obtained in Preparation Example 1 (75 mg, 0.113 mmol), the compound obtained in Preparation Example 2 (763 mg, 0.905 mmol) and 4-dimethylaminopyridine (20.7 mg, 0.169 mmol) were dissolved in 6 ml of N,N-dimethylformamide, and 1-[3-(dimethylamino)propyl]-ethylcarbodiimide hydrochloride (173.5 mg, 0.905 mmol) was added thereto, followed by stirring the mixture at room temperature for a day. After the reaction was completed, the reaction mixture was extracted with 65 ml of dichloromethane and washed with saturated NaHCO$_3$ (30 ml) and water several times. The organic layer thus obtained was dried over Na$_2$SO$_4$, concentrated under a reduced pressure, and purified by column chromatography (dichloromethane:methanol=9:1), to obtain the title compound having four introduced side chains at its skeleton as a white foamy solid (278 mg).

$^1$H-NMR (CDCl$_3$): δ 1.01(s, 9H), 1.35-1.40(m, 168H), 2.19-2.27(m, 32H), 2.66(brs, 16H), 2.78-2.93(m, 2H), 3.31-3.58(m, 32H), 3.63-3.92(m, 2H), 4.01(brs, 1H), 4.23(brs, 1H), 4.88-5.12(m, 2H), 7.16-7.58(m, 25H, aromatic), 7.94 (brs, 8H), 8.51(brs, 8H), 11.35(brs, 8H)

MS (MALDI-TOF) m/z 3987.73(M$^+$+Na-2)

EXAMPLE 1

Preparation of Alditol Derivative having Eight Guanidine Groups I

<1-1> Removal of t-butyldiphenylsilane Protecting Group

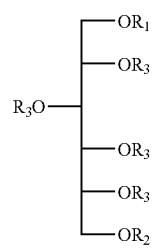

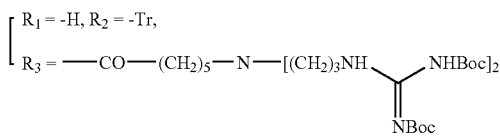

The compound obtained in Preparation Example <6-3> (100 mg, 0.0285 mmol) was dissolved in 3.5 ml of tetrahydrofurane, and 25 μl (0.0854 mmol) of 1 mol tetrabutylammoniumfluoride tetrahydrofurane solution was added thereto, followed by stirring the mixture at room temperature for 10 hrs. After the reaction was completed, the reaction mixture was diluted with 60 ml of dichloromethane, and washed with brine and water several times. The organic layer was dried over $Na_2SO_4$, concentrated under a reduced pressure, and purified by column chromatography (dichloromethane:methanol=9:1), to obtain the title compound as a sticky white solid (74 mg).

$^1$H-NMR (CDCl$_3$): δ 1.25-1.68(m, 184H), 2.35-2.45(m, 32H), 3.40(brs, 4H), 3.42(brs., 16H), 4.05-4.42(m, 2H), 5.21 (brs, 1H), 5.53(brs, 1H), 7.29-7.41(m, 15H), 8.50(brs., 8H), 11.49(brs., 8H)

MS (MALDI-TOF) m/z 3295.4532(M$^+$+Na)

<1-2> Introduction of Carbobenzoxy Protecting Groups (Cbz)

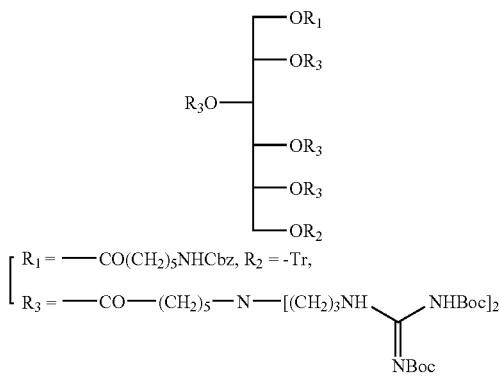

The compound obtained in Example <1-1> (85 mg, 0.0026 mmol), the compound obtained in Preparation Example 4 (17.2 mg, 0.065 mmol) and 4-dimethylamino pyridine (1.6 mg, 0.013 mmol) were dissolved in 2.5 ml of N,N-dimethylformamide, and 1-[3-(dimethylamino)propyl]-ethylcarbodiimide hydrochloride (12.5 mg, 0.065 mmol) was added thereto, followed by stirring the mixture at room temperature for 1 day. After the reaction was completed, the reaction mixture was extracted with dichloromethane (40 ml), and washed with a saturated $NaHCO_3$ aqueous solution (60 ml) and water several times. The organic layer was dried over $Na_2SO_4$, concentrated under a reduced pressure, and purified by column chromatography (dichloromethane:methanol=9:1), to obtain the title compound having introduced four side chains at its skeleton as a white foamy solid (65 mg).

$^1$H-NMR (CDCl$_3$): δ 1.25-1.70(m, 184H), 2.28-2.44(m, 32H), 3.41-3.66(m, 22H), 4.08-4.44(m, 4H), 5.07(s, 2H), 5.24(brs., 1H), 5.56(brs., 1H), 7.25-7.38(m, 20H), 8.50(brs., 8H), 11.50(brs., 8H)

<1-3> Removal of Carbobenzoxy Protecting Groups from Terminal Amine Groups of Side Chains

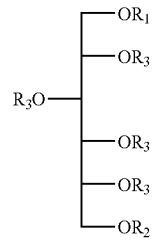
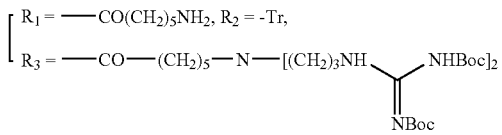

The compound obtained in Example <1-2> (50 mg, 0.0105 mmol) was dissolved in 3 ml of a methanol and dichloromethane mixture (9:1), and Pd/C (40 mg) was added thereto. A hydrogen gas (1 atm) was introduced therein, and the mixture was stirred at room temperature for 1 day and filtered through celite to remove the Pd/C catalyst. The filtrate thus obtained was concentrated under a reduced pressure to obtain the title compound as a white sticky solid (44 mg)

$^1$H-NMR (CD$_3$OD): δ 1.28-1.66(m, 184H), 1.89-2.00(m, 16H), 2.34(brs., 4H), 2.96-3.23(m, 16H), 3.47(brs., 16H), 3.57-3.68(m, 2H), 4.01-4.21(m, 2H), 4.66-4.70(m, 2H), 5.22 (brs., 1H), 5.58(brs., 1H), 7.27-7.39(m, 15H)

<1-4> Introduction of Fluorescent Tag

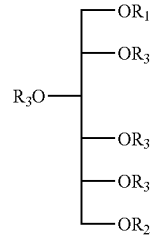
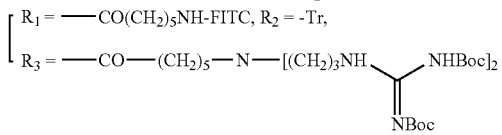

The compound obtained in Example <1-3> (40 mg, 0.0118 mmol) was dissolved in 3 ml of a tetrahydrofuran and ethanol mixture (3:2), and fluoroscein-5-isocianate (5.8 mg, 0.0153 mmol) and triethylamine (4.9 μl, 0.0355 mmol) were added thereto, followed by stirring the mixture at room temperature for 1 day. After the reaction was completed, the reaction mixture was subjected to column chromatography (dichloromethane:methanol=10:1), to obtain the title compound as a light green syrup (30 mg).

$^1$H-NMR (CDCl$_3$): δ 1.25-1.74(m, 184H), 2.05-2.31(m, 32H), 3.58(brs., 18H), 4.02-4.24(m, 2H), 4.56(brs., 1H), 5.22 (brs., 1H), 5.41(brs., 1H), 6.59-6.81(m, 6H), 7.26-7.39(m, 15H), 7.69-7.79(m, 2H), 7.99(brs., 1H), 8.49(brs., 8H), 11.38 (brs., 8H)

<1-5> Removal of N-Boc and O-trityl Protecting Groups from N,N'-di-Boc-guanidine Groups

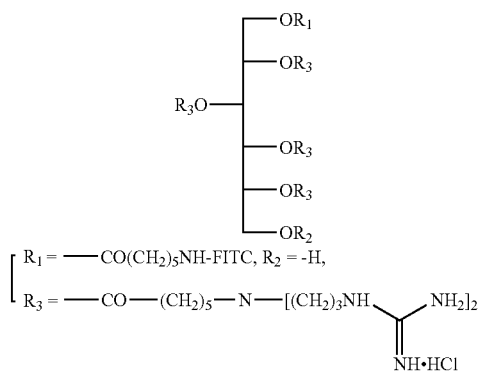

The compound obtained in Example <1-4> (25 mg, 0.0066 mmol) was dissolved in 1 ml of ethyl acetate, and 4 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2) and freeze-drying, to obtain the title compound as a light-green foamy solid (12 mg).

$^1$H-NMR (CD$_3$OD): δ 1.45-1.88(m, 40H), 2.03(brs., 16H), 2.34(brs., 16H), 3.34(brs., 16H, merged with CD$_3$OD peak), 3.67-3.79(m, 2H), 4.03-4.23(m, 2H), 5.17-5.46(m, 4H), 6.52-6.73(m, 5H), 7.21-7.32(m, 1H), 7.33-7.41(m, 1H), 7.81-7.95 (m, 2H), 8.28(brs., 1H)

MS (MALDI-TOF) m/z 1950.87(M$^+$+Na)

EXAMPLE 2

Preparation of Alditol Derivative having Eight Guanidine Groups

<2-1> Removal of t-butyldiphenylsilane Protecting Group

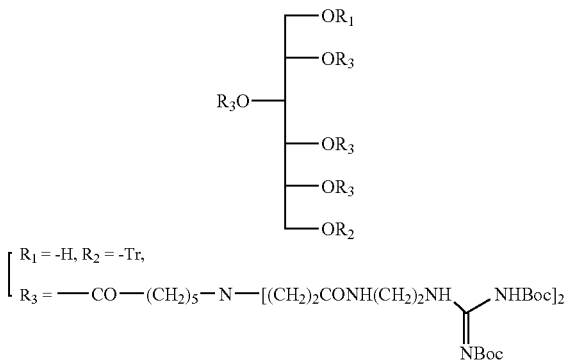

The compound obtained in Preparation Example 7 (250 mg, 0.063 mmol) was dissolved in 5 ml of tetrahydrofurane, and 1 mol tetrabutylammoniumfluoride tetrahydrofurane solution (64 μl, 0.220 mmol) was added thereto, which was stirred at room temperature for 15 hrs. After the reaction was completed, the reaction mixture was diluted with 65 ml of dichloromethane, and washed with brine and water several times. The organic layer was dried over Na$_2$SO$_4$, concentrated under a reduced pressure, and purified by column chromatography (dichloromethane:methanol=9:1), to obtain the title compound as a sticky white solid (188 mg).

$^1$H-NMR (CDCl$_3$): δ 1.18-1.54(m, 168H), 2.11-2.41(m, 32H), 2.67(brs., 16H), 3.30-3.45(m, 32H), 3.76-3.89(m, 2H), 4.02-4.24(m, 2H), 4.81-4.99(m, 2H), 7.18-7.34(m, 25H, aromatic), 8.13(brs., 8H), 8.50(brs., 8H), 11.35(brs., 8H)

MS (MALDI-TOF) m/z 3750.27(M$^+$+Na)

<2-2> Introduction of Carbobenzoxy Protecting Groups (Cbz)

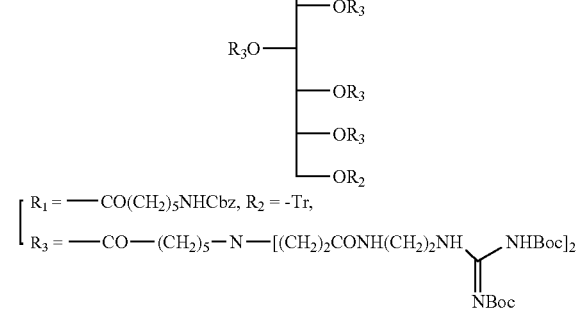

The compound obtained in Example <2-1> (90 mg, 0.0241 mmol), the compound obtained in Preparation Example 4 (16 mg, 0.0603 mmol) and 4-dimethylamino pyridine 2 mg, 0.0096 mmol) were dissolved in 2.5 ml of N,N-dimethylformamide, and 1-[3-(dimethylamino)propyl]-ethylcarbodiimide hydrochloride (1.5 mg, 0.0603 mmol) was added thereto, followed by stirring the mixture at room temperature for 1 day. After the reaction was completed, the reaction mixture was extracted with dichloromethane (50 ml), and washed with a saturated NaHCO$_3$ aqueous solution (75 ml) and water several times. The organic layer thus obtained was dried over Na$_2$SO$_4$, concentrated under a reduced pressure, and purified by column chromatography (dichloromethane:methanol=9:1), to obtain the title compound having introduced four side chains at its skeleton as a white foamy solid (69 mg).

$^1$H-NMR (CDCl$_3$): δ 1.18-1.54(m, 174H), 2.24-2.28(m, 32H), 2.65(brs., 16H), 3.16(brs., 4H), 3.30-3.43(m, 32H), 3.71-3.88(m, 2H), 4.11-4.28(m, 4H), 4.76-4.81(m, 2H), 4.99 (s, 2H), 7.18-7.32(m, 20H, aromitic), 7.89(brs., 8H), 8.48 (brs., 8H), 11.34(brs., 8H)

MS (MALDI-TOF) m/z 3997.27(M$^+$+Na)

<2-3> Removal of Carbobenzoxy Protecting Groups from Terminal Amine Groups of Side Chains

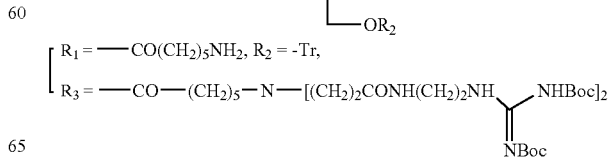

The compound obtained in Example <2-2> (60 mg, 0.0150 mmol) was dissolved in 3 ml of a methanol and dichloromethane mixture (9:1), and Pd/C (42 mg) was added thereto. A hydrogen gas (1 atm) was introduced therein, and the mixture was stirred at room temperature for 1 day and filtered through celite to remove the Pd/C catalyst. The filtrate thus obtained was to concentrated under a reduced pressure to obtain the title compound as a white sticky solid (50 mg)

$^1$H-NMR (CD$_3$OD): δ 1.28-1.67(m, 174H), 2.26-2.59(m, 32H), 2.87(brs., 16H), 2.92-3.00(m, 4H), 3.31-3.50(m, 32H), 3.82-3.91(m, 2H), 4.06-4.22(m, 4H), 4.79-4.89(m, 2H, partially merged with CD$_3$OD peak), 7.32-7.47(m, 15H)

<2-4> Introduction of Fluorescent Tag

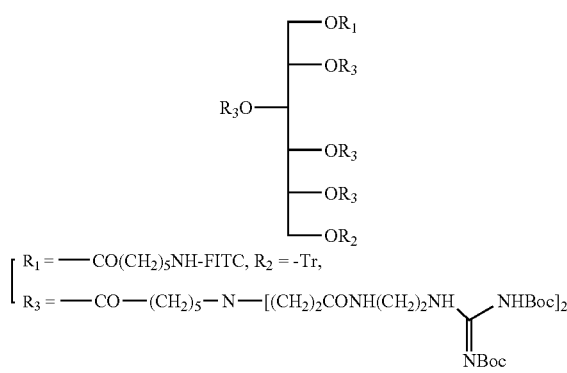

The compound obtained in Example <2-3> (45 mg, 0.0117 mmol) was dissolved in 3 ml of a tetrahydrofuran:ethanol mixture (3:2), and fluoroscein-5-isocianate (5.9 mg, 0.0152 mmol) and triethylamine (4.8 μl, 0.0351 mmol) were added thereto, followed by stirring the mixture at room temperature for 1 day. After the reaction was completed, the reaction mixture was subjected to column chromatography (dichloromethane:methanol=10:1), to obtain the title compound as a light green syrup (32 mg).

$^1$H-NMR (CDCl$_3$): δ 1.19-1.60(m, 174H), 2.16-2.34(m, 32H), 3.06-3.14(m, 16H), 3.35-3.48(m, 32H), 3.78-3.91(m, 4H), 4.10-4.22(m, 2H), 4.88-4.93(m, 2H), 6.64-6.91(m, 6H), 7.27-7.38(m, 15H), 7.88-8.21(m, 10H), 8.55(brs., 8H), 11.41 (brs., 8H)

<2-5> Removal of N-Boc and O-trityl Protecting Groups from N,N'-di-Boc-guanidine Groups

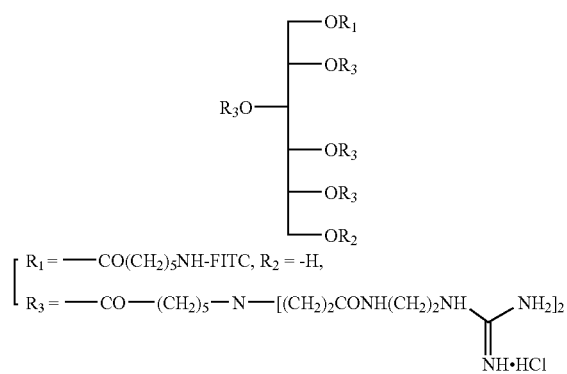

The compound obtained in Example <2-4> (27 mg, 0.0063 mmol) was dissolved in 1 ml of ethyl acetate, and 4 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2) and freeze-drying, to obtain the title compound as a light-green foamy solid (14.3 mg).

$^1$H-NMR (CD$_3$OD): δ 1.28-1.88(m, 46H), 2.43(brs., 16H), 3.28-3.44(m, 48H, partially merged with CD$_3$OD peak), 3.88-3.98(m, 2H), 4.03-4.28(m, 4H), 6.57-6.84(m, 6H), 7.81 (brs., 2H), 8.33(brs., 1H)

MS (MALDI-TOF) m/z 2407.34(M$^+$+Na)

EXAMPLE 3

Preparation of Alditol Derivative Conjugated with Doxorubicin

<3-1> Introduction of Doxorubicin

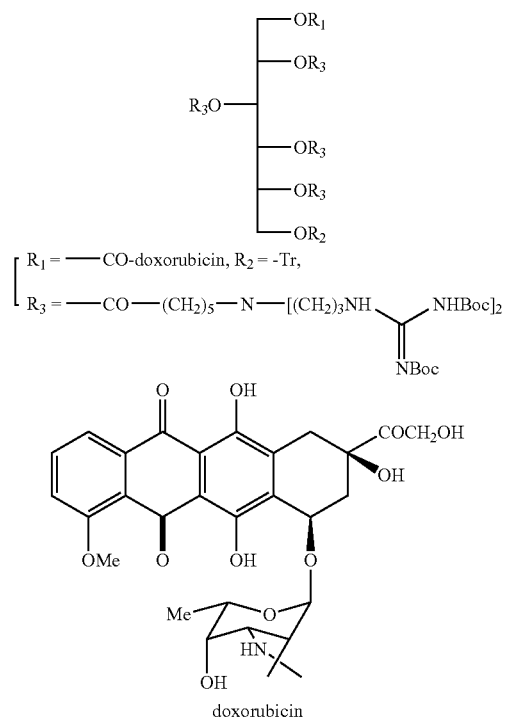

The compound obtained in Example <1-1> (55 mg, 0.0168 mmol) and p-nitrophenylchloromate (94 mg, 0.047 mmol) were dissolved in 4 ml of dichloromethane, and pyridine (68 μl, 0.084 mmol) was added thereto, followed by stirring the mixture at room temperature for 2 days. After the reaction was completed, the reaction mixture was dried in a vacuum oven to remove the solvent and dissolved in N,N-dimethylformamide (3 ml), and triethylamine (14.2 μl, 0.1 mmol) and doxorubicin-hydrochloride (13.7 mg, 0.0235 mmol; Waco Pure Chemical Industries, Ltd.) were added thereto, followed the darkroom treatment of the resulting mixture with stirring at room temperature for 1 day. The resulting solution was concentrated, and the residue thus obtained was purified by column chromatography (dichloromethane:methanol=10:1), to obtain the title compound as a red sticky solid (40.5 mg).

$^1$H-NMR (CDCl$_3$): δ 1.36-1.77(m, 184H), 2.18-2.56(m, 32H), 3.47-3.66(m, 18H), 3.78(s, 3H), 4.07-4.33(m, 8H), 4.67-5.44(m, 11H), 7.23-7.47(m, 15H), 7.59-7.64(m, 1H), 7.73-7.91(m, 2H), 8.51(brs., 8H), 11.47(brs., 8H)

MS (MALDI-TOF) m/z 3867.5923(M$^+$+Na+2)

<3-2> Removal of N-Boc and O-trityl Protecting Groups from N,N'-di-Boc-guanidine Groups

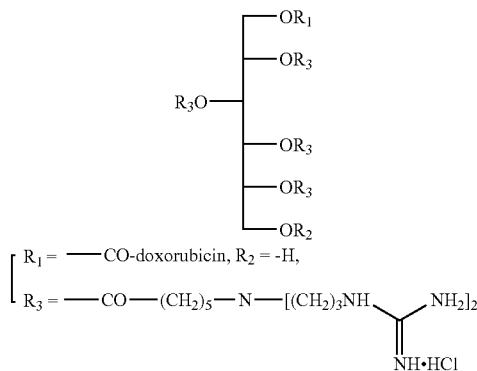

The compound obtained in Example <3-1> (40 mg, 0.0102 mmol) was dissolved in 1 ml of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2), to obtain the title compound as a red compound (17.4 mg).

$^1$H-NMR (CD$_3$OD): δ 1.19-1.88(m, 40H), 2.23(brs., 32H), 2.45(brs., 8H), 3.30-3.53(m, 17H, partially merged with CD$_3$OD peak at 3.31), 3.82-4.33(m, 10H), 4.45-4.68(m, 3H), 5.11-5.23(m, 2H), 7.44(brs., 1H), 7.78(brs., 1H), 7.96-8.01 (m, 1H)

MS (MALDI-TOF) m/z 2020.8277(M$^+$+Na+2)

EXAMPLE 4

Preparation of Alditol Derivative Conjugated with Paclitaxel

<4-1> Introduction of Paclitaxel

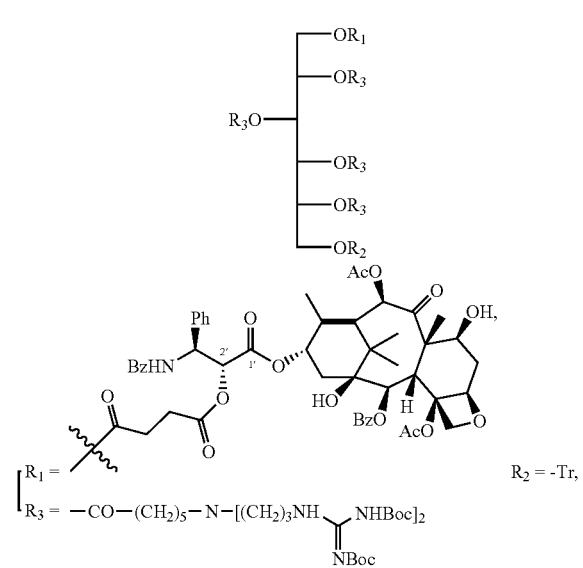

The compound obtained in Example <1-1> (55 mg, 0.0168 mmol), the paclitaxel derivative obtained in Preparation Example 5 (108 mg, 0.115 mmol) and 4-dimethylaminopyridine (20.7 mg, 0.169 mmol) were dissolved in 6 ml of dichloromethane, and 1-[3-(dimethylamino)propyl]-ethylcarodiimide hydrochloride (173.5 mg, 0.905 mmol) was added thereto, followed by stirring the mixture at room temperature for 2 days. After the reaction was completed, the reaction mixture was extracted with ethylacetate (65 ml) and washed with a saturated NaHCO$_3$ aqueous solution (30 ml) and water several times. The organic layer thus obtained was dried over Na$_2$SO$_4$, concentrated under a reduced pressure, and purified by column chromatography (dichloromethane:methanol=10:1), to obtain the title compound having introduced four side chains at its skeleton as a white foamy solid (278 mg).

$^1$H-NMR (CDCl$_3$): δ 1.21-1.48(m, 184H), 1.67-2.04(m, 18H), 2.13-2.72(m, 44H), 3.08-3.42(m, 16H), 3.68(s, 2H), 3.88(brs., 2H), 4.03-4.44(m, 6H), 4.77-5.10(m, 4H), 5.18-5.25(m, 2H), 5.55-5.73(m, 2H), 5.90(brs., 1H), 6.10-6.29(m, 2H), 7.18-7.54(m, 28H), 8.12(brs., 2H), 8.49(brs., 8H), 11.49 (brs., 8H)

<4-2> Removal of N-Boc and O-trityl Protecting Groups from N,N'-di-Boc-guanidine Groups

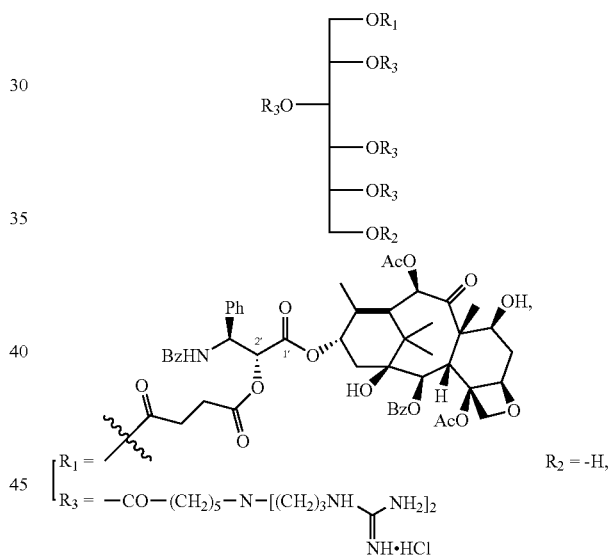

The compound obtained in Example <4-1> (170 mg, 0.0405 mmol) was dissolved in ethyl acetate, and 6.5 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2), to obtain the title compound as a red compound (83.5 mg).

$^1$H-NMR (CD$_3$OD): δ 1.44-1.81(m, 48H), 2.10-2.23(m, 30H), 2.39-2.88(21H), 3.30-3.53(m, 20H, partially merged with CD$_3$OD peak at 3.31), 3.62-3.93(m, 5H), 4.11-4.32(m, 4H), 4.67-4.88(m, 2H), 5.02-5.41(m, 4H), 5.88(brs., 1H), 6.32(brs., 1H), 7.22-8.17(m, 15H);

MS (MALDI-TOF) m/z 2372.5631(M$^+$+Na)

EXAMPLE 5

Preparation of Alditol Derivative Conjugated with Paclitaxel

<5-1> Removal of 6-O-trityl Protecting Group

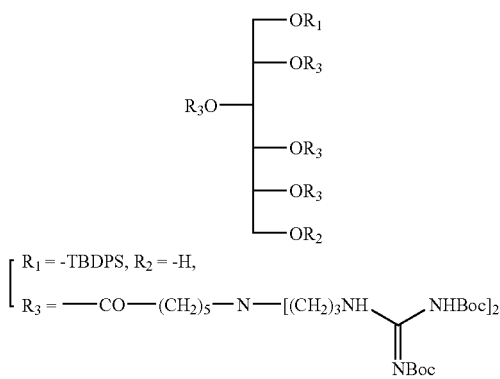

The compound obtained in Example <6-3> (125 mg, 0.0327 mmol) was dissolved in 3 ml of dichloromethane, and a catalytic amount of trifluoroacetic acid was added dropwise thereto, followed by stirring the mixture at room temperature for 12 hrs. After the reaction was completed, the reaction mixture was diluted with 30 ml of dichlorimethane and washed with water several times. The organic layer thus obtained was dried over $Na_2SO_4$, concentrated under a reduced pressure, and the residue was purified by column chromatography (dichloromethane:methanol=9:1), to obtain the title compound (87 mg).

$^1$H-NMR ($CDCl_3$): δ 1.05(s, 9H), 1.25-1.74(m, 184H), 2.04-2.53(m, 34H), 3.34(brs., 2H), 3.45-3.47(m, 16H), 3.81-4.02(m, 2H), 4.11-4.32(m, 4H), 4.84(brs., 1H), 5.56(brs., 1H), 5.72(brs., 1H), 7.32-7.41(m, 6H, aromatic), 7.65-7.67 (m, 4H, aromatic), 8.50(brs., 8H), 11.48(brs., 8H)

MS (MALDI-TOF) m/z 3292.45($M^+$+Na)

<5-2> Protection of Amino Groups with Carbobenzoxy Group (Cbz)

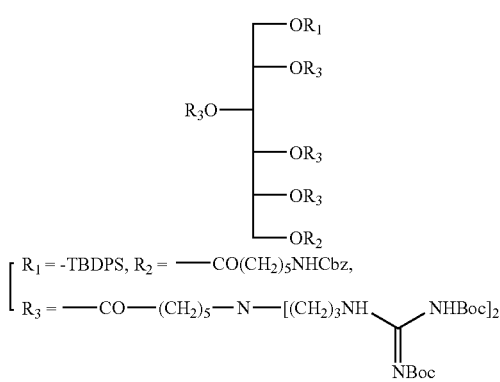

The compound obtained in Example <5-1> (85 mg, 0.0229 mmol), the compound obtained in Preparation Example 4 (12.1 mg, 0.0458 mmol) and 4-dimethylaminopyridine (1.6 mg, 0.0413 mmol) was dissolved in 2.5 ml of N,N-dimethylformamide, and 1-[3-(dimethylamino)propyl]-ethylcarodiimide hydrochloride (8.7 mg, 0.0458 mmol) was added thereto, followed by stirring the mixture at room temperature for 1 day. After the reaction was completed, the reaction mixture was extracted with 30 ml of dichloromethane and washed with a saturated $NaHCO_3$ aqueous solution (75 ml) and water several times. The organic layer thus obtained was dried over $Na_2SO_4$, concentrated under a reduced pressure, and purified by column chromatography (dichloromethane:methanol=9:1), to obtain the title compound as a white foamy solid (62 mg).

$^1$H-NMR ($CD_3OD$): δ 1.05(s, 9H), 1.25-1.70(m, 184H), 2.28-2.48(m, 32H), 3.11-3.26(m, 2H), 3.55(brs., 16H), 3.68-3.88(m, 2H), 4.06-4.22(m, 2H), 4.78-4.85(m, 2H), 5.07(s, 2H), 5.67(brs., 1H), 5.87(brs., 1H), 7.27-7.39(m, 6H), 7.41-7.68(m, 4H), 8.50(brs., 8H), 11.48(brs., 8H)

<5-3> Removal of t-butyldiphenylsilane Protecting Group

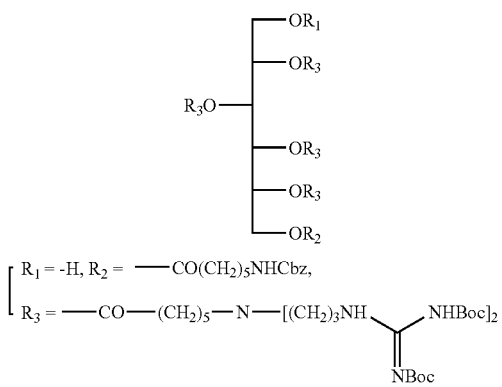

The compound obtained in Preparation Example <5-2> (60 mg, 0.0170 mmol) was dissolved in 3.5 ml of tetrahydrofurane, and 1 mol tetrabutylammoniumfluoride tetrahydrofurane solution (30 μl, 0.1024 mmol) was added thereto, followed by stirring the mixture at room temperature for 10 hrs. After the reaction was completed, the reaction mixture was diluted with 35 ml of dichloromethane, and washed with brine and water several times. The organic layer was dried over $Na_2SO_4$, concentrated under a reduced pressure, and purified by column chromatography (dichloromethane:methanol=9:1), to obtain the title compound as a sticky white solid (51 mg).

$^1$H-NMR ($CDCl_3$): δ 1.22-1.73(m, 184H), 2.02-2.50(m, 32H), 3.21(brs., 4H), 3.44-3.48(m, 16H), 3.87(brs., 1H), 4.12-4.52(m, 5H), 4.93(brs., 1H), 5.08(s, 2H), 5.12-5.39(m, 2H), 7.34(brs., 5H, aromatic), 8.51(brs., 8H), 11.48(brs., 8H)

MS (MALDI-TOF) m/z 3300.2081($M^+$+Na)

<5-4> Introduction of Paclitaxel

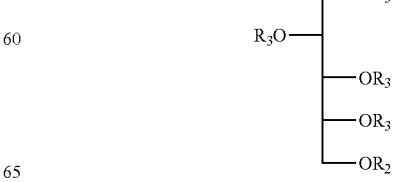

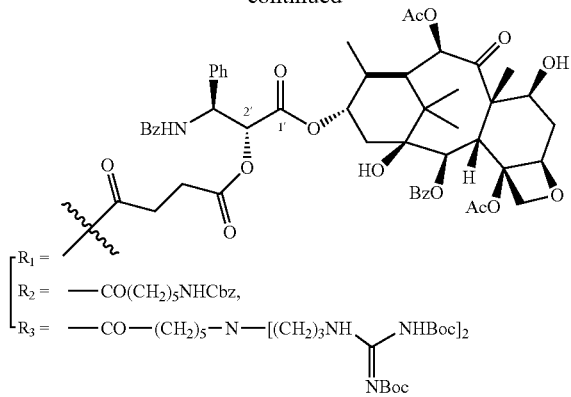

R₁ = [squiggle]
R₂ = —CO(CH₂)₅NHCbz,
R₃ = —CO—(CH₂)₅—N—[(CH₂)₃NH–C(NHBoc)=NBoc]₂

The compound obtained in Example <5-3> (50 mg, 0.0152 mmol), a paclitaxel derivative obtained in Preparation Example 5 (108 mg, 0.115 mmol) and 4-dimethylaminopyridine (28.5 mg, 0.0305 mmol) were dissolved in 2.6 ml of dichloromethane, and 1-[3-(dimethylamino)propyl]-ethylcarodiimide hydrochloride (6.4 mg, 0.0305 mmol) was added thereto, followed by stirring the mixture at room temperature for 2 days. After the reaction was completed, the reaction mixture was extracted with ethylacetate and washed with a saturated NaHCO₃ aqueous solution and water several times. The organic layer thus obtained was dried over Na₂SO₄, concentrated under a reduced pressure, and purified by column chromatography (dichloromethane:methanol=10:1), to obtain the title compound having introduced four side chains at its skeleton as a white foamy solid (47 mg).

¹H-NMR (CDCl₃): δ 1.28-1.67(m, 190H), 1.89-2.04(m, 18H), 2.21-2.45(m, 32H), 2.63-2.81(12H), 3.11-3.48(m, 18H), 3.82(brs., 2H), 4.13-4.41(m, 8H), 4.82-5.23(m, 5H), 5.57-5.82(m, 3H), 6.03(brs., 1H), 6.11-6.32(m, 2H), 7.26-7.50(m, 18H), 8.22(brs., 2H), 8.50(brs., 8H), 11.49(brs., 8H)

<5-5> Removal of Carbobenzoxy Protecting Groups from Terminal Amine Groups of Side Chains

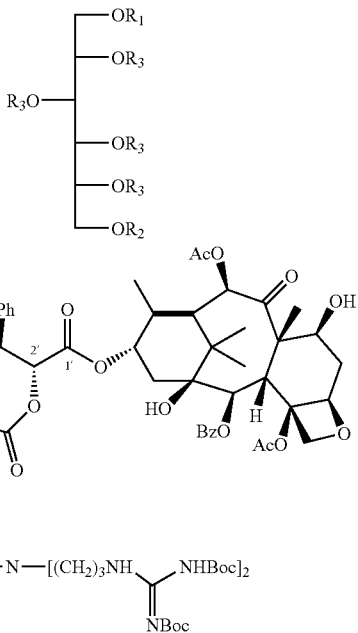

R₁ = [squiggle]
R₂ = —CO(CH₂)₅NH₂,
R₃ = —CO—(CH₂)₅—N—[(CH₂)₃NH–C(NHBoc)=NBoc]₂

The compound obtained in Example <5-4> (60 mg, 0.0150 mmol) was dissolved in 3 ml of a methanol:dichloromethane mixture (9:1), and Pd/C (42 mg) was added thereto. A hydrogen gas (1 atm) was introduced therein, and the mixture was stirred at room temperature for 1 day and filtered through celite to remove the Pd/C catalyst. The filtrate thus obtained was concentrated under a reduced pressure to obtain the title compound as a white sticky solid (50 mg)

<5-6> Introduction of Fluorescent Tag

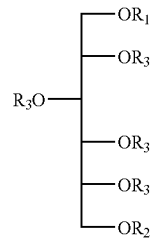

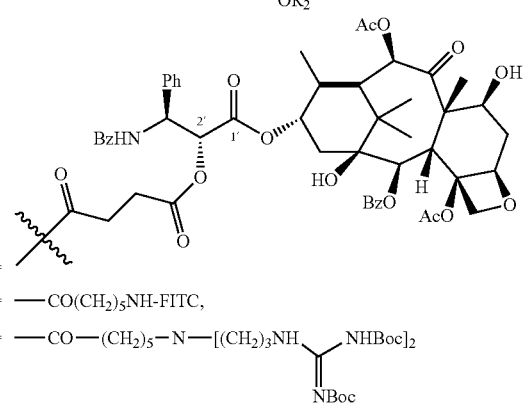

R₁ = [squiggle]
R₂ = —CO(CH₂)₅NH-FITC,
R₃ = —CO—(CH₂)₅—N—[(CH₂)₃NH–C(NHBoc)=NBoc]₂

The compound obtained in Example <5-5> (45 mg, 0.0110 mmol) was dissolved in 3 ml, of a tetrahydrofuran:ethanol mixture (3:2), and fluoroscein-5-isocianate (5.2 mg, 0.0133 mmol) and triethylamine (7.7 μl, 0.0552 mmol) were added thereto, followed by conducting the darkroom treatment of the mixture with stirring at room temperature for 1 day. After the reaction was completed, the reaction mixture was subjected to column chromatography (dichloromethane:methanol=10:1), to obtain the title compound as a light green syrup (27.6 mg).

¹H-NMR (CDCl₃): δ 1.21-1.78(m, 204H), 2.02-2.38(m, 48H), 3.02-3.41(m, 20H, merged with CD₃OD peak at 3.31), 3.44-4.19(m, 6H), 4.51-4.63(m, 4H), 5.11-5.36(m, 3H), 5.68-5.82(m, 2H), 6.33(brs., 1H), 6.66-6.81(m, 6H), 7.26-7.73(m, 16H), 7.98-8.31(m, 2H)

<5-7> Removal of N-Boc Protecting Groups from N,N'-di-Boc-guanidine Groups

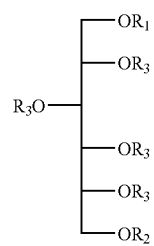

-continued

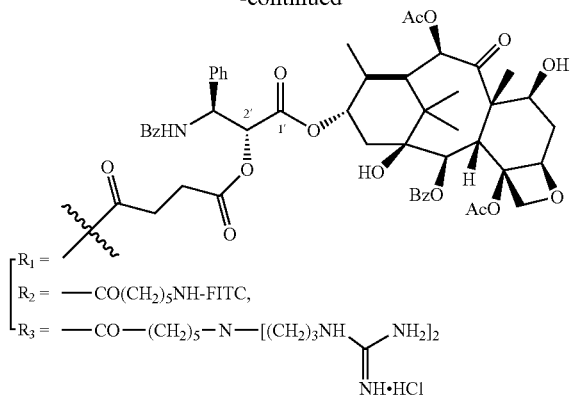

The compound obtained in Example <5-6> (27 mg, 0.0060 mmol) was dissolved in 1 ml of ethyl acetate, and 2 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2) and freeze-drying, to obtain the title compound as a light-green foamy solid (13.2 mg).

$^1$H-NMR (CD$_3$OD): δ 1.22-1.73(m, 184H), 2.02-2.50(m, 32H), 3.21(brs., 4H), 3.44-3.48(m, 16H), 3.87(brs., 1H), 4.12-4.52(m, 5H), 4.93(brs., 1H), 5.08(s, 2H), 5.12-5.39(m, 2H), 7.34(brs., 5H, aromatic), 8.51(brs., 8H), 11.48(brs., 8H)

MS (MALDI-TOF) m/z 2875.4287(M$^+$+Na)

EXAMPLE 6

Preparation of Alditol Derivative Conjugated with Fatty Acids

<6-1> Introduction of Fatty Acids

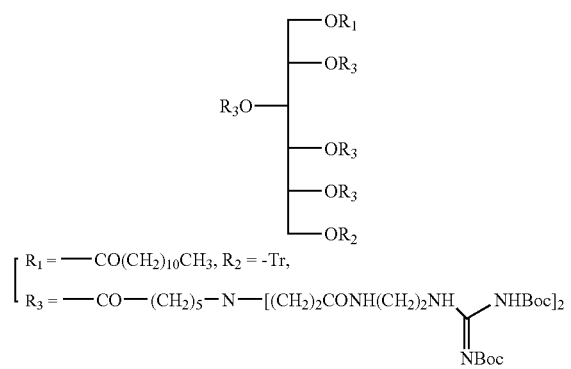

The compound obtained in Example <2-1> (40 mg, 0.0107 mmol), dodecanoic acid (Sigma-Aldrich Inc.) (4.3 mg, 0.0214 mmol) and 4-dimethylaminopyridine (0.5 mg, a catalytic amount) were dissolved in 2.5 ml of dichloromethane, and 1-[3-(dimethylamino)propyl]-ethylcarodiimide hydrochloride (4.1 mg, 0.0214 mmol) was added thereto, followed by stirring the mixture at room temperature for 1 day. After the reaction was completed, the reaction mixture was extracted with ethylacetate and washed with a saturated NaHCO$_3$ aqueous solution and water several times. The organic layer thus obtained was dried over Na$_2$SO$_4$, concentrated under a reduced pressure, and purified by column chromatography (dichloromethane:methanol=9:1), to obtain the title compound having introduced four side chains at its skeleton as a white foamy solid (32 mg).

$^1$H-NMR (CDCl$_3$): δ 1.25-1.60(m, 191H), 2.33-2.40(m, 32H), 2.71(brs., 16H), 3.38-3.53(m, 32H), 4.01-4.34(m, 4H), 4.78(brs., 2H), 5.22-5.38(m, 2H), 7.26-7.39(m, 15H), 7.99 (brs., 8H), 8.58(brs., 8H), 11.42(brs., 8H)

MS (MALDI-TOF) m/z 3948.8154(M$^+$+Na)

<6-2> Removal of N-Boc and O-trityl Protecting Groups from N,N'-di-Boc-guanidine Groups

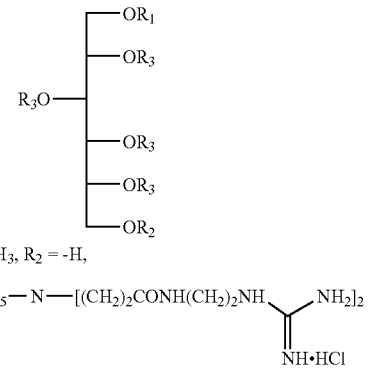

The compound obtained in Example <6-1> (30 mg, 0.0076 mmol) was dissolved in 1 ml of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to freeze drying to obtain the title compound as a white foamy solid (15.3 mg).

$^1$H-NMR (CD$_3$OD): δ 1.25(s, 44H), 1.30-1.88(m, 43H), 2.28-2.50(m, 16H), 2.88(brs., 16H), 3.02(brs., 2H), 3.32-3.56 (m, 32H, partially merged with CD$_3$OD peak), 4.00-4.22(m, 4H)

MS (MALDI-TOF) m/z 2088.8975(M$^+$+Na)

EXAMPLE 7

Preparation of Alditol Derivative Conjugated with Fatty Acids

<7-1> Introduction of Fatty Acids

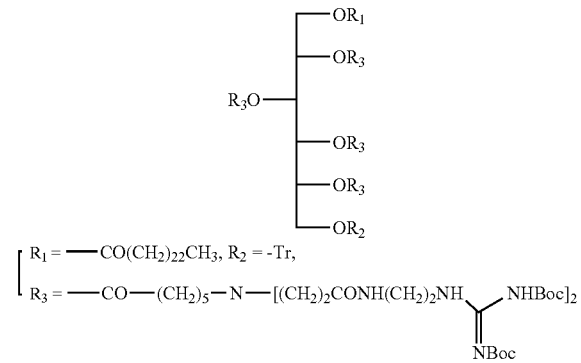

The compound obtained in Example <2-1> (40 mg, 0.0107 mmol), tetracosanoic acid (Acros Organics) (8.1 mg, 0.0214 mmol) and 4-dimethylaminopyridine (0.5 mg, catalytic amount) were dissolved in 2.5 ml of dichloromethane, and 1-[3-(dimethylamino)propyl]-ethylcarodiimide hydrochloride (4.1 mg, 0.0214 mmol) was added thereto, followed by stirring the mixture at room temperature for 1 day. After the reaction was completed, the reaction mixture was extracted with ethylacetate and washed with a saturated NaHCO$_3$ aqueous solution and water several times. The organic layer thus obtained was dried over Na$_2$SO$_4$, concentrated under a reduced pressure, and purified by column chromatography (dichloromethane:methanol=9:1), to obtain the title compound having introduced four side chains at its skeleton as a white foamy solid (31 mg).

$^1$H-NMR (CDCl$_3$): δ 1.24-1.61(m, 215H), 2.22-2.39(m, 32H), 2.71(brs., 16H), 3.38-3.52(m, 32H), 4.00-4.32(m, 4H), 4.81(brs., 2H), 5.18-5.32(m, 2H), 7.25-7.38(m, 15H), 8.02 (brs., 8H), 8.58(brs., 8H), 11.42(brs., 8H)

MS (MALDI-TOF) m/z 4118.0681(M$^+$+Na)

<7-2> Removal of N-Boc and O-trityl Protecting Groups from N,N'-di-Boc-guanidine Groups

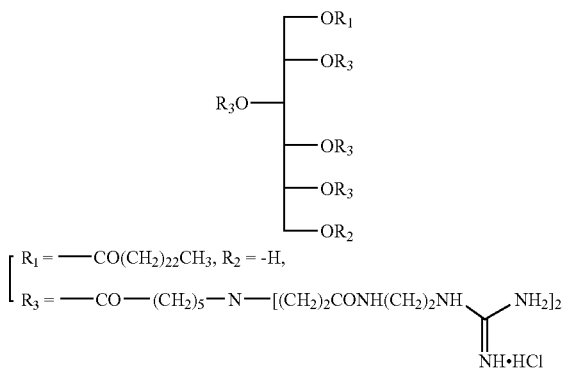

The compound obtained in Example <7-1> (28 mg, 0.0068 mmol) was dissolved in 1 ml of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure, washed with a diethylether and methanol mixture (20:1) to remove non-polar impurities, and freeze-dried, to obtain the title compound as a white foamy solid (14.4 mg).

$^1$H-NMR (CD$_3$OD): δ 1.22(brs., 59H), 1.38-1.91(m, 40H), 2.22-2.39(m, 16H), 2.71-2.93(m, 16H), 3.30-3.51(m, 32H, partially merged with CD$_3$OD peak), 4.01-4.22(m, 4H)

MS (MALDI-TOF) m/z 2257.8542(M$^+$+Na)

EXAMPLE 8

Preparation of Alditol Derivative Conjugated with Fatty Acids

<8-1> Introduction to Fatty Acids

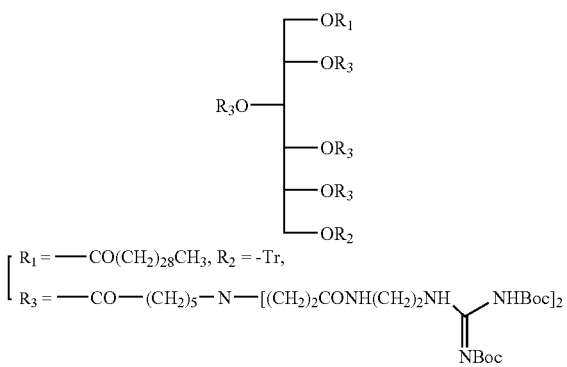

The compound obtained in Example <2-1> (35 mg, 0.0093 mmol), triacontanoic acid (Sigma-Aldrich Inc.) (8.5 mg, 0.0187 mmol) and 4-dimethylaminopyridine (0.5 mg, catalytic amount) were dissolved in 2.5 ml of dichloromethane, and 1-[3-(dimethylamino)propyl]-ethylcarodiimide hydrochloride (3.6 mg, 0.0187 mmol) was added thereto, followed by stirring the mixture at room temperature for 1 day. After the reaction was completed, the reaction mixture was extracted with ethylacetate and washed with a saturated NaHCO$_3$ aqueous solution and water several times. The organic layer thus obtained was dried over Na$_2$SO$_4$, concentrated under a reduced pressure, and purified by column chromatography (dichloromethane:methanol=9:1), to obtain the title compound having introduced four side chains at its skeleton as a white foamy solid (30 mg).

$^1$H-NMR (CDCl$_3$): δ 1.17-1.40(m, 227H), 2.12-2.42(m, 32H), 2.77(brs., 16H), 3.31-3.45(m, 32H), 3.98-4.38(m, 4H), 4.76-4.88(m, 2H), 5.21-5.38(m, 2H), 7.20-7.30(m, 15H), 7.88(brs., 8H), 8.49(brs., 8H), 11.35(brs., 8H)

<8-2> Removal of N-Boc and O-trityl Protecting Groups from N,N'-di-Boc-guanidine Groups

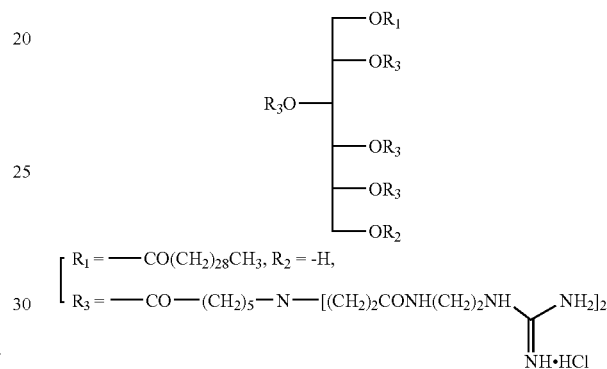

The compound obtained in Example <8-1> (27 mg, 0.0064 mmol) was dissolved in 1 ml of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure, washed with a diethylether and methanol mixture (20:1) to remove non-polar impurities, and freeze-dried, to obtain the title compound as a white foamy solid (11.6 mg).

$^1$H-NMR (CD$_3$OD): δ 1.17-1.40(m, 227H), 2.12-2.42(m, 32H), 2.77(brs., 16H), 3.31-3.45(m, 32H), 3.98-4.38(m, 4H), 4.76-4.88(m, 2H), 5.21-5.36(m, 2H), 7.20-7.30(m, 15H), 7.88(brs., 8H), 8.49(brs., 8H), 11.35(brs., 8H)

MS (MALDI-TOF) m/z 2342.6512(M$^+$+Na)

EXAMPLE 9

Preparation of Alditol Derivative Conjugated with Amino Acids

<9-1> Removal of 6-O-trityl Protecting Group

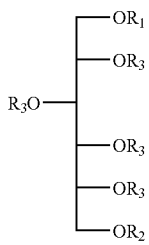

-continued

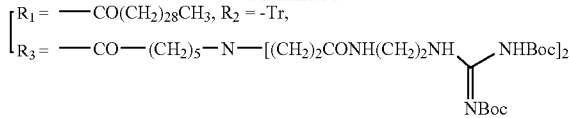

The compound obtained in Example <8-1> (50 mg, 0.0120 mmol) was dissolved in 2.6 ml of dichloromethane, and a catalytic amount of trifluoroacetic acid was added dropwise thereto, followed by stirring the mixture at room temperature for 12 hrs. After the reaction was completed, the reaction mixture was diluted with 30 ml of dichlorimethane and washed with water several times. The organic layer thus obtained was dried over $Na_2SO_4$, concentrated under a reduced pressure, and the residue was purified by column chromatography (dichloromethane:methanol=9:1), to obtain the title compound (33.5 mg).

$^1$H-NMR (CDCl$_3$): δ 1.21-1.44(m, 224H), 2.02-2.43(m, 36H), 2.65-2.74(m, 16H), 3.32-3.44(m, 32H), 3.98-4.33(m, 4H), 4.72-4.80(m, 2H), 5.18-5.26(m, 2H), 7.24-7.36(m, 15H), 7.89(brs., 8H), 8.50(brs., 8H), 11.33(brs., 8H)

<9-2> Introduction of Histidine Having Amine Groups Protected with Carbobenzoxy Groups

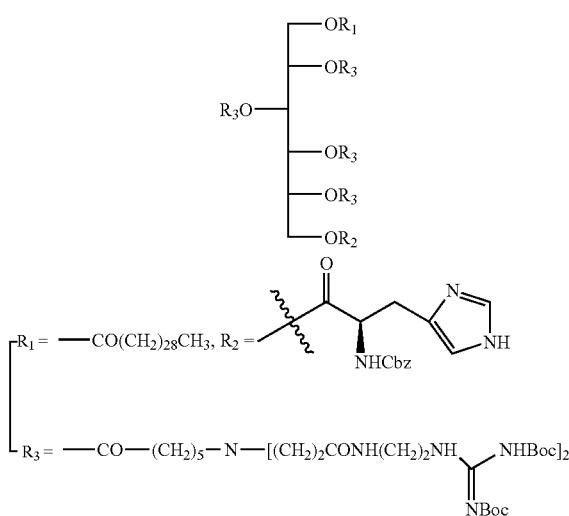

The compound obtained in Example <9-1> (30 mg, 0.0084 mmol), N-carbobenzoxy-L-histidine (TCI Organic Chemicals)(5.3 mg, 0.0185 mmol) and 4-dimethylaminopyridine (0.5 mg, catalytic amount) was dissolved in 2.5 ml of dichloromethane, and 1-[3-(dimethylamino)propyl]-ethylcarodiimide hydrochloride (3.5 mg, 0.0185 mmol) was added thereto, followed by stirring the mixture at room temperature for 2 days. After the reaction was completed, the reaction mixture was extracted with dichloromethane and washed with a saturated NaHCO$_3$ aqueous solution and water several times. The organic layer thus obtained was dried over Na$_2$SO$_4$, concentrated under a reduced pressure, and purified by column chromatography (dichloromethane:methanol=10:1), to obtain having introduced four side chains at its skeleton as a white foamy solid (26 mg).

$^1$H-NMR (CD$_3$OD): δ 1.26-1.60(m, 227H), 2.22-2.48(m, 32H), 2.72(brs., 16H), 3.39-3.53(m, 32H), 4.01-4.27(m, 4H), 4.82(brs., 2H), 5.01(s, 2H), 5.54-5.63(m, 2H), 7.27-7.34(m, 5H), 8.02(brs., 9H), 8.38(brs., 8H), 11.42(s, 8H)

<9-3> Removal of N-Boc Protecting Groups from N,N'-di-Boc-guanidine Groups

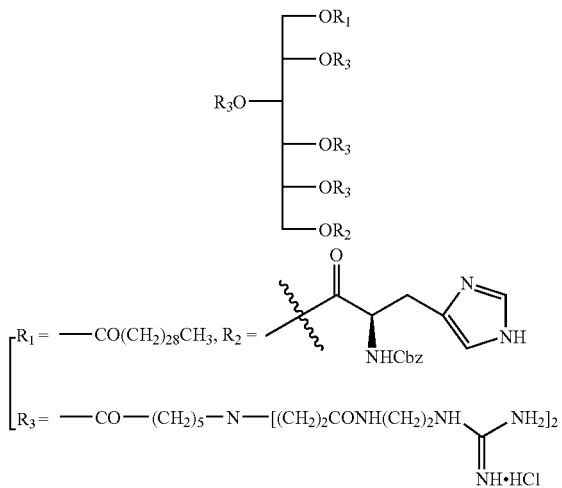

The compound obtained in Example <9-2> (25 mg, 0.0062 mmol) was dissolved in 1 ml of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure, washed with a diethylether and methanol mixture (20:1) to remove non-polar impurities, and freeze-dried, to obtain the title compound as a white foamy solid (11.1 mg).

$^1$H-NMR (CD$_3$OD): δ 1.23(brs, 59H), 1.30-1.92(m, 40H), 2.18-2.37(m, 16H), 2.88-3.01(m, 16H), 3.30-3.56(m, 32H, partially merged with CD$_3$OD peak), 4.01-4.28(m, 4H), 7.26-7.48(m, 6H)

MS (MALDI-TOF) m/z 2613.0431(M$^+$+Na)

EXAMPLE 10

Preparation of Alditol Derivative Conjugated with Fatty Acids

<10-1> Introduction of Fatty Acids

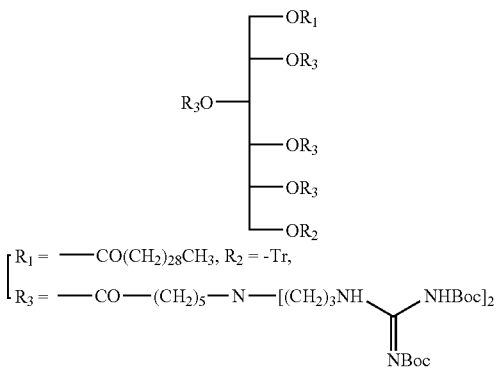

The compound obtained in Example <1-1> (35 mg, 0.0106 mmol), triacontanoic acid (12.1 mg, 0.0267 mmol) and 4-dimethylaminopyridine (0.5 mg, catalytic amount) were dissolved in 2.5 ml of dichloromethane, and 1-[3-(dimethylamino)propyl]-ethylcarodiimide hydrochloride (5.2 mg, 0.0267 mmol) was added thereto, followed by stirring the mixture at room temperature for 2 days. After the reaction was completed, the reaction mixture was extracted with ethylacetate and washed with a saturated NaHCO₃ aqueous solution and water several times. The organic layer thus obtained was dried over Na₂SO₄, concentrated under a reduced pressure, and purified by column chromatography (dichloromethane:methanol=9:1), to obtain the title compound having introduced four side chains at its skeleton as a white foamy solid (30 mg).

¹H-NMR (CDCl₃): δ 1.17-1.70(brs., 227H), 2.23-2.55(m, 32H), 3.22-3.58(m, 18H), 4.02-4.26(m, 2H), 4.82-5.02(m, 2H), 7.27-7.38(m, 15H, aromatic), 8.50(brs., 8H), 11.48(brs., 8H)

MS (MALDI-TOF) m/z 3729.0976(M⁺+Na)

<10-2> Removal of N-Boc and O-trityl Protecting Groups from N,N'-di-Boc-guanidine Groups

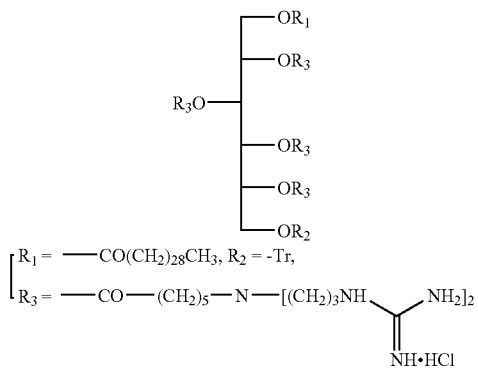

The compound obtained in Example <10-1> (28 mg, 0.0075 mmol) was dissolved in 1 ml of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure, washed with a diethylether and methanol mixture (20:1) to remove non-polar impurities, and freeze-dried, to obtain the title compound as a white foamy solid (10.8 mg).

¹H-NMR (CD₃OD): δ 1.19-1.24(m, 59H), 1.32-1.96(m, 40H), 2.02-2.67(m, 32H), 3.03-3.64(m, 20H, partially merged with CD₃OD peak at 3.31)

MS (MALDI-TOF) m/z 1884.5143(M⁺+Na)

EXAMPLE 11

Preparation of Inositol Derivative

<11-1>: Removal of Acetonide Protecting Groups

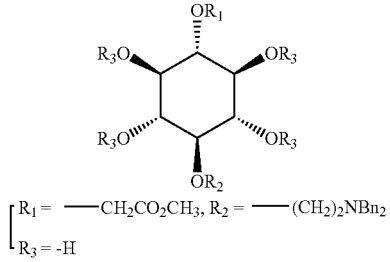

4-O-(2-N,N-dibenzylaminoethyl)-1-O-(methoxycarbonyl-methyl)-2,3:5,6-di-O-isopropylidene-scyllo-inositol (Korean Patent No. 10-0578732; 148.5 mg, 0.267 mmol) was dissolved in 3 ml of a mixture of dichloromethane and methanol (4:1), and 0.1 ml of ethyl acetate saturated with HCl gas was added dropwise thereto, followed by stirring the mixture at room temperature for 1 day. The resulting mixture was concentrated under a reduced pressure and dried in a vacuum oven, to obtain the title compound as a white solid (127 mg).

¹H-NMR (CD₃OD): δ 3.09-3.10(m, 2H), 3.35-3.39(m, 6H), 3.77(s, 3H, —COOMe), 4.15(t, J=4.9 Hz, 2H), 4.40-4.55(m, 6H, -inositol ring proton), 7.49-7.55(m, 10H, 2 Ph)

MS (FAB) m/z 498.22(M⁺+Na)

<11-2> Introduction of Side Chains by Acylation

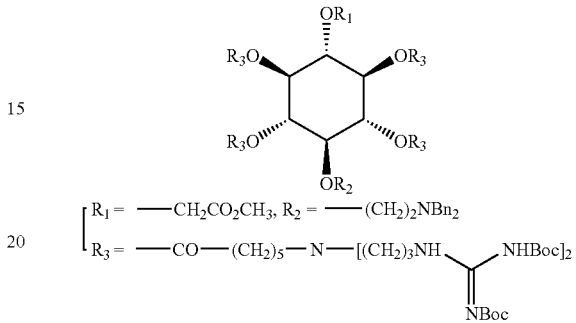

The compound obtained in Example <11-1> (50 mg, 0.105 mmol), the compound obtained in Preparation Example <2-4> (400 mg, 0.548 mmol), and 4-dimethylamino pyridine (18 mg, 0.141 mmol) were dissolved in 4 ml of N,N-dimethylformamide, and 1-[3-(dimethylamino)propyl]-ethylcarbodiimide hydrochloride (106 mg, 0.55 mmol) were added thereto, followed by stirring the mixture at room temperature for 1 day. After the reaction was completed, the reaction mixture was extracted with dichloromethane, and the extract was washed several times with saturated NaHCO₃ and water. The organic layer was dried over Na₂SO₄, concentrated under a reduced pressure, and purified by column chromatography (dichloromethane:methanol=9:1), to obtain the title compound having introduced four side chains at its skeleton as a white foamy solid (216 mg).

¹H-NMR (CDCl₃): δ 1.22-1.70(m, 184H), 1.98-2.58(m, 30H), 3.15-3.73(m, 29H), 4.09-5.05(m, 8H), 7.24-7.27(m, 10H, Ph), 8.45(br. s, 8H), 11.44(br. s, 8H)

MS (MALDI-TOF) m/z 3346.70(M⁺+Na)

<11-3> Removal of Benzyl Protecting Groups and Introduction of Fluorescent Tag

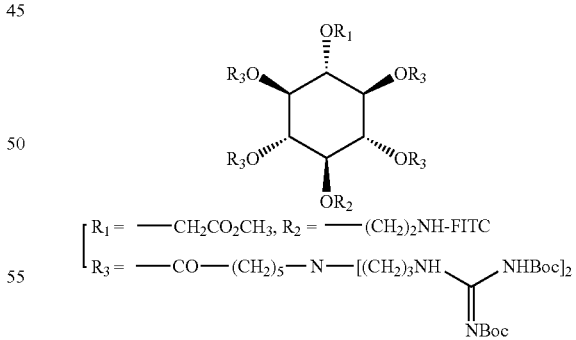

The compound obtained in Example <11-2> (100 mg, 0.0301 mmol) was dissolved in 6 ml of a methanol:dichloromethane mixture (9:1), and Pd/C (100 mg) was added thereto. A hydrogen gas (1 atm) was introduced therein, and the mixture was stirred at room temperature for 1 day and filtered through celite to remove the Pd/C catalyst. The filtrate was concentrated under a reduced pressure, and the residue thus obtained was dissolved in 3 ml of a tetrahydrofuran:ethanol mixture (3:2), and fluoroscein-5-isociante (8.3 mg, 0.0218 mmol) and triethylamine (7 μl, 0.0477 mmol) were added thereto, followed by stirring the mixture at room temperature for 1 day. After the reaction was completed, the reaction mixture was subjected to column chromatography (dichloromethane:methanol=10:1), to obtain the title compound as a light green syrup (33.2 mg).

$^1$H-NMR (CDCl$_3$): δ 1.23-1.68(m, 184H), 2.00-2.76(m, 38H), 3.44-3.84(m, 10H), 4.08-4.61(m, 5H), 4.85-5.51(m, 10H), 6.59-6.78(m, 6H), 7.18-7.20(m, 2H), 8.03(br. s, 8H), 8.18-8.20(m, 1H), 8.52(br. s, 8H), 11.53(br. s, 8H)

MS (MALDI-TOF) m/z 3555.90(M$^+$+Na)

<11-4> Removal of N-Boc Protecting Groups from N,N'-di-Boc-guanidine Groups

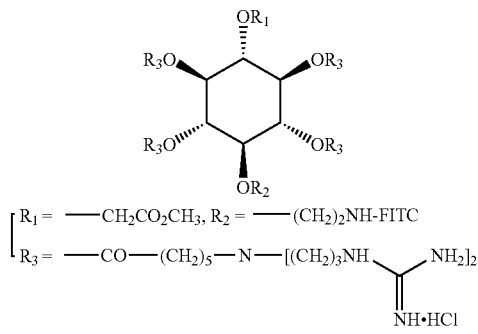

The compound obtained in Example <11-3> (23 mg, 0.0057 mmol) was dissolved in 5 ml of ethyl acetate, and 2 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2), to obtain the title compound as a light-green solid (7.1 mg).

$^1$H-NMR (CD$_3$OD): δ 1.25-1.75(m, 40H), 2.07-2.16(m, 21H), 2.49-2.61(m, 10H) 2.97(s, 2H), 3.77-3.91(m, 14H), 4.11-4.56(m, 6H), 6.56-6.68(m, 6H), 7.16-7.18(m, 2H), 8.19-8.21(br. s, 1H)

MS (MALDI-TOF) m/z 1933.98(M$^+$+Na)

EXAMPLE 12

Preparation of Inositol Derivative

<12-1> Introduction of Side Chains by Acylation

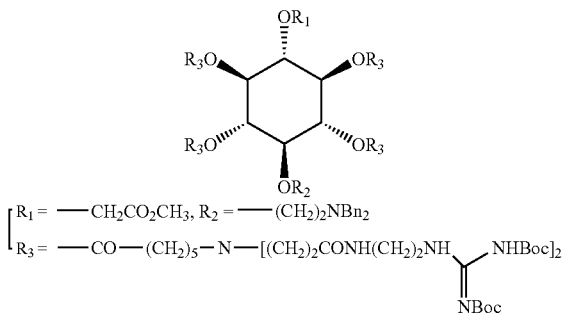

The compound obtained in Example <11-1> (15 mg, 0.0315 mmol), the compound obtained in Example <3-4> (132.5 mg, 0.157 mmol), and 4-dimethylamino pyridine (6 mg, 0.0473 mmol) were dissolved in 3 ml of N,N-dimethylformamide, and 1-[3-(dimethylamino)propyl]-ethylcarbodiimide hydrochloride (31 mg, 0.16 mmol) were added thereto, followed by stirring the mixture at room temperature for 1 day. After the reaction was completed, the reaction mixture was extracted with dichloromethane, and the extract was washed several times with saturated NaHCO$_3$ and water. The organic layer was dried over Na$_2$SO$_4$, concentrated under a reduced pressure, and purified by column chromatography (dichloromethane:methanol=9:1), to obtain the title compound having introduced four side chains at its skeleton as a white foamy solid (50 mg).

$^1$H-NMR (CDCl$_3$): δ 1.22-1.57(m, 168H), 2.31-2.70(m, 52H), 3.27-3.71(m, 39H), 4.11-5.27(m, 8H), 7.24-7.28(m, 10H, Ph), 7.92(br. s, 8H), 8.54(br. s, 8H) 11.4(br. s, 8H)

MS (MALDI-TOF) m/z 3555.90(M$^+$+Na)

<12-2> Removal of Benzyl Protecting Groups and Introduction of Fluorescent Tag

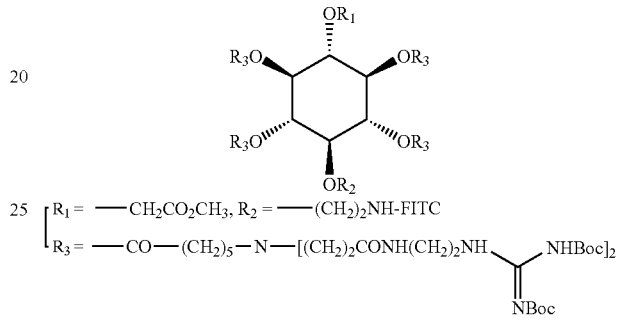

The compound obtained in Example <12-1> (30 mg, 0.0075 mmol) was dissolved in 4 ml of a methanol:dichloromethane mixture (9:1), and Pd/C (100 mg) was added thereto. A hydrogen gas (1 atm) was introduced therein, and the mixture was stirred at room temperature for 1 day and filtered through celite to remove the Pd/C catalyst. The filtrate was concentrated under a reduced pressure, and the residue thus obtained was dissolved in 2 ml of a tetrahydrofuran:ethanol mixture (3:2), and fluoroscein-5-isocianate (8.3 mg, 0.0218 mmol) and triethylamine (3 μl, 0.02 mmol) were added thereto, followed by stirring the mixture at room temperature for 1 day. After the reaction was completed, the reaction mixture was subjected to column chromatography (dichloromethane:methanol=10:1), to obtain the title compound as a light green syrup (15 mg).

$^1$H-NMR (CDCl$_3$): δ 1.26-1.86(m, 168H), 2.00-2.18(m, 52H), 3.07-3.49(m, 35H), 3.65-4.11(m, 6H), 5.31(s, 2H), 6.55-6.80(m, 6H), 7.22(br. s, 2H), 8.03(br. s, 2H), 8.03(br. s, 8H), 8.52(br. s, 9H), 11.49(br. s, 8H)

MS (MALDI-TOF) m/z 4012.30(M$^+$+Na)

<12-3> Removal of N-Boc Protecting Groups from N,N'-di-Boc-guanidine Groups

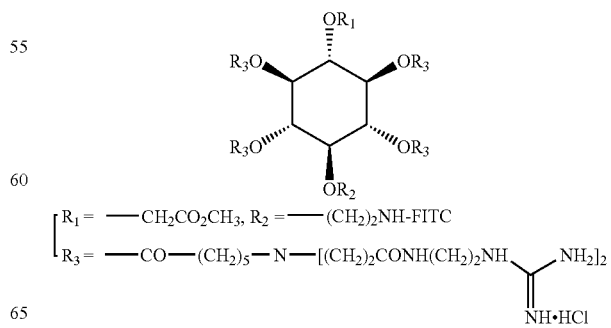

The compound obtained in Example <12-2> (30 mg, 0.0075 mmol) was dissolved in 5 ml of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2), to obtain the title compound as a light-green solid (15 mg).

$^1$H-NMR (D$_2$O): δ 1.30-1.74(m, 24H), 2.49-2.88(m, 18H), 3.26-3.90(m, 69H) 4.10-4.54(m, 8H), 6.54-6.69(m, 6H), 7.15-7.19(m, 2H), 8.23-8.25(m, 7H)

MS (MALDI-TOF) m/z 2409.12(M$^+$+Na)

EXAMPLE 13

Preparation of Inositol Derivative

<13-1> Introduction of Side Chains by Acylation

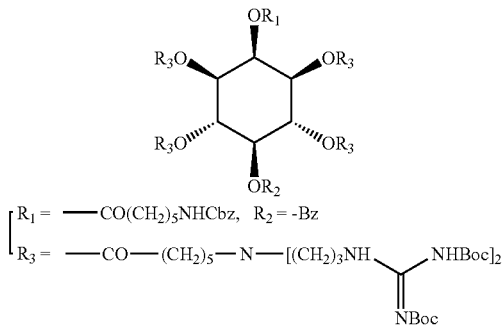

4-O-benzoyl-1-O-(6-benzyloxycarbonyl-aminohexanoyl)-myo-inositol (Korean Patent No. 10-0578732; 47.5 mg, 0.0893 mmol), the compound obtained in Preparation Example <2-4> (330 mg, 0.452 mmol) and 4-dimethylamino pyridine (16 mg, 0.126 mmol) were dissolved in 4 ml of N,N-dimethylformamide, and 1-[3-(dimethylamino)propyl]-ethylcarbodiimide hydrochloride (88 mg, 0.46 mmol) were added thereto, followed by stirring the mixture at room temperature for 1 day. After the reaction was completed, the reaction mixture was extracted with dichloromethane, and the extract was washed several times with saturated NaHCO$_3$ and water. The organic layer was dried over Na$_2$SO$_4$, concentrated under a reduced pressure, and purified by column chromatography (dichloromethane:methanol=9:1), to obtain the title compound having introduced four side chains at its skeleton as a white foamy solid (199.5 mg).

$^1$H-NMR (CDCl$_3$): δ 1.27-1.71(m, 190H), 2.03-2.49(m, 36H), 2.95-3.08(m, 6H), 3.44-3.70(m, 20H), 4.29-6.57(m, 8H), 7.26-7.43(m, 6H), 7.83-8.00(m, 4H), 8.49(br. s, 8H), 11.48(br. s, 8H)

MS (MALDI-TOF) m/z 3402.65(M$^+$+Na)

<13-2> Removal of Benzyl Protecting Groups and Introduction of Fluorescent Tag

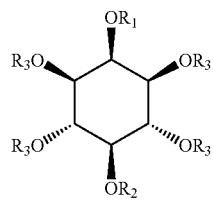

-continued

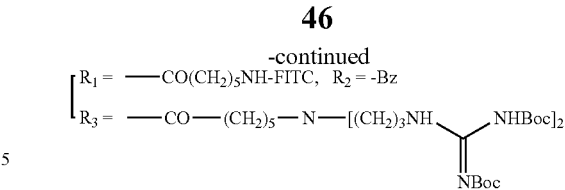

The compound obtained in Example <13-1> (100 mg, 0.0295 mmol) was dissolved in 6 ml of a methanol:dichloromethane mixture (9:1), and Pd/C (100 mg) was added thereto. A hydrogen gas (1 atm) was introduced therein, and the mixture was stirred at room temperature for 1 day and filtered through celite to remove the Pd/C catalyst. The filtrate was concentrated under a reduced pressure, and the residue thus obtained was dissolved in 3 ml of a tetrahydrofuran:ethanol mixture (3:2), and fluoroscein-5-isocianate (8.3 mg, 0.0218 mmol) and triethylamine (7 μl, 0.0477 mmol) were added thereto, followed by stirring the mixture at room temperature for 1 day. After the reaction was completed, the reaction mixture was subjected to column chromatography (dichloromethane:methanol=10:1), to obtain the title compound as a light green syrup (47.6 mg).

$^1$H-NMR (CDCl$_3$): δ 1.22-1.65(m, 190H), 1.92-2.32(m, 30H), 2.85-3.42(m, 14H), 3.64-4.61(m, 10H), 5.28-5.57(m, 6H), 6.58-7.94(m, 14H), 8.48(br. s, 8H), 11.38(br. s, 8H)

MS (MALDI-TOF) m/z 3657.90(M$^+$+Na)

<13-3> Removal of N-Boc Protecting Groups from N,N'-di-Boc-guanidine Groups

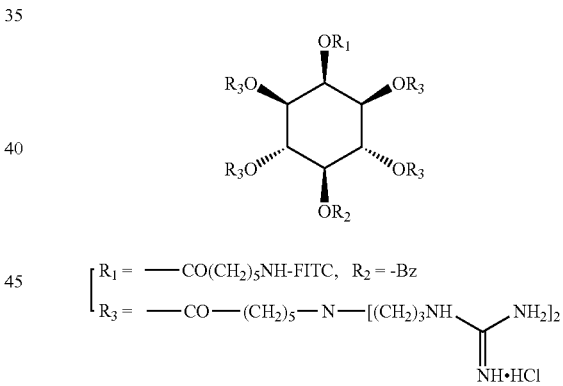

The compound obtained in Example <13-2> (30 mg, 0.0083 mmol) was dissolved in 5 mg of ethyl acetate, and 2.5 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2), to obtain the title compound as a light-green solid (11.3 mg).

$^1$H-NMR (D$_2$O): δ 1.32-1.80(m, 46H), 2.01-2.15(m, 33H), 2.34-2.88(m, 24H), 3.90-4.34(m, 12H), 5.38-5.72(m, 11H), 7.63-8.15(m, 14H)

MS (MALDI-TOF) m/z 2056.12(M$^+$+Na)

EXAMPLE 14

Preparation of Inositol Derivative

<14-1> Introduction of Side Chains by Acylation

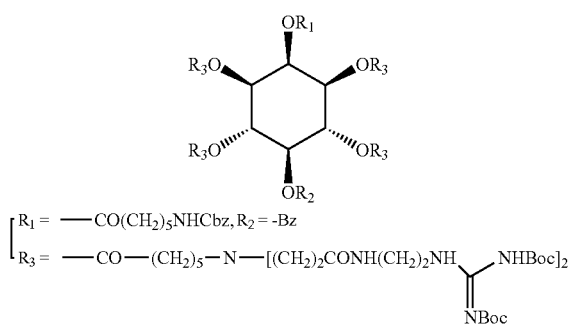

4-O-benzoyl-1-O-(6-benzyloxycarbonyl-aminohexanoyl)-myo-inositol (42 mg, 0.0789 mmol), the compound obtained in Preparation Example <3-4> (400 mg, 0.473 mmol) and 4-dimethylamino pyridine (14 mg, 0.11 mmol) were dissolved in 3 ml of N,N-dimethylformamide, and 1-[3-(dimethylamino)propyl]-ethylcarbodiimide hydrochloride (91 mg, 0.473 mmol) were added thereto, followed by stirring the mixture at room temperature for 1 day. After the reaction was completed, the reaction mixture was extracted with dichloromethane, and the extract was washed several times with saturated $NaHCO_3$ and water. The organic layer was dried over $Na_2SO_4$, concentrated under a reduced pressure, and purified by column chromatography (dichloromethane:methanol=9:1), to obtain the title compound having introduced four side chains at its skeleton as a white foamy solid (51.2 mg).

$^1$H-NMR ($CDCl_3$): δ 1.26-1.69(m, 174H), 2.00-2.04(m, 12H), 2.13-2.37(m, 25H), 2.70-2.72(m, 13H), 3.24-3.80(m, 36H), 4.87-5.31(m, 10H), 7.42-7.55(m, 5H), 7.95-8.07(m, 8H), 8.58(br. s, 8H), 11.41(br. s, 8H)

MS (MALDI-TOF) m/z 3858.02($M^+$+Na)

<14-2> Removal of Benzyl Protecting Groups and Introduction of Fluorescent Tag

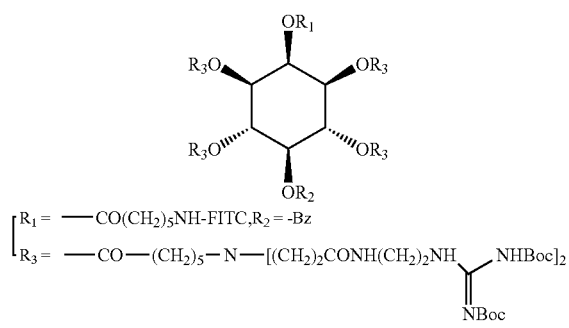

The compound obtained in Example <14-1> (45 mg, 0.0117 mmol) was dissolved in 4 ml of a methanol:dichloromethane mixture (9:1), and Pd/C (100 mg) was added thereto. A hydrogen gas (1 atm) was introduced therein, and the mixture was stirred at room temperature for 1 day and filtered through celite to remove the Pd/C catalyst. The filtrate was concentrated under a reduced pressure, and the residue thus obtained was dissolved in 2 ml of a tetrahydrofuran:ethanol mixture (3:2), and fluoroscein-5-isocianate (8.3 mg, 0.0218 mmol) and triethylamine (5 μl, 0.0324 mmol) were added thereto, followed by stirring the mixture at room temperature for 1 day. After the reaction was completed, the reaction mixture was subjected to column chromatography (dichloromethane:methanol=10:1), to obtain the title compound as a light green syrup (35.3 mg).

$^1$H-NMR ($CDCl_3$): δ 1.25-1.73(m, 174H), 1.99-2.31(m, 37H), 2.65-2.90(m, 10H), 3.18-3.39(m, 12H), 3.47-4.28(m, 15H), 4.64-5.33(m, 16H), 6.63-8.52(m, 14H), 11.39(br. s, 1H)

MS (MALDI-TOF) m/z 4113.30($M^+$+Na)

<14-3> Removal of N-Boc Protecting Groups from N,N'-di-Boc-guanidine Groups

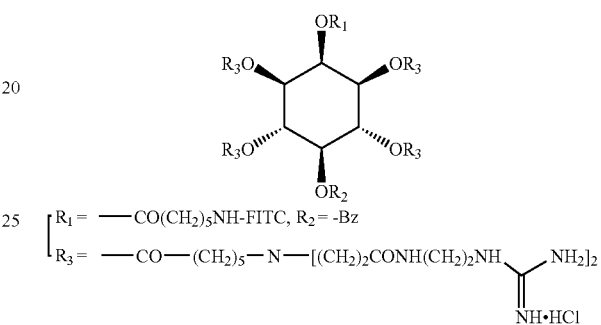

The compound obtained in Example <14-2> (20 mg, 0.005 mmol) was dissolved in 5 ml of ethyl acetate, and 2 ml of ethyl acetate saturated with HCl gas was added dropwise thereto, followed by stirring the mixture at room temperature for 1 day. After the reaction was completed, the reaction mixture was concentrated under a reduced pressure and washed with a diethylether and methanol mixture (20:1) to remove non-polar impurities. The resulting solution was subjected to MPLC chromatography (water containing 0.1% trifluoroacetic acid:acetonitrile=1:1 to 1:2), to obtain the title compound as a light-green solid (7.9 mg).

$^1$H-NMR ($D_2O$): δ 1.08-1.32(m, 30H), 1.97-2.47(m, 9H), 2.82-3.06(m, 12H), 3.17-3.48(m, 56H), 3.63-4.35(m, 10H), 5.30-5.51(m, 3H), 7.15-8.17(m, 14H)

MS (MALDI-TOF) m/z 2512.02($M^+$+Na)

TEST EXAMPLE 1

Measurement of Membrane Permeability

The permeability through a cell membrane and a nuclear membrane of each of the compounds having $NH_2$ groups selectively conjugated with FITC prepared in the above Examples, was measured and compared with that of FITC-conjugated arginine nonamer (Fl-$Arg_9$, FITC-$Arg_9$; Peptron) which is known to efficiently permeate through biological membranes as well as with that of an intermediate having no guanidine group.

A cover glass was placed on a dish plate and mouse macrophage RAW264.7 cells (ATCC T1B-71) were cultured thereon. The cells were stabilized in DMEM (Dulbecco's modified Eagle's medium) supplemented with 10% FBS for 24 hrs, and cultured in a serum-free medium for 24 hrs to starve the cells. Thereafter, the cells were treated with Fl-$Arg_9$, and then with each of the compounds obtained in Examples 1 and 2 at a concentration of 10 μM for 3 min at a constant temperature (23~25° C.), followed by washing the plate with PBS (phosphate buffer solution) three times. The cells were fixed by treating with ethanol for a day, and a section of the collected surface was observed with a confocal microscope.

Further, The cells were treated with doxorubicin (Woca Pure Chemical Industries, Ltd.) alone, and then with each of the compounds obtained in Examples 1, 3, 5, 11, 12, 13 and 14 at a concentration of 10 μM for 15 min at a constant temperature (23 ~25° C.). The treated cells were washed 5 times with cold PBS (4° C.), followed by observing a section of the collected surface with a confocal microscope equipped with Ar laser (wavelength 458 nm) to detect the fluorescent signal at a magnification of ×400, without conducting the step of cell fixation. The results are shown in FIG. 1.

In FIG. 1, item (1) shows the fluorescent images of RAW264.7 cells which were treated with Fl-Arg$_9$ (a), the compound obtained in Example 2 (b) and the compound obtained in Example 1 (c), respectively; item (2) shows the fluorescent images of RAW264.7 cells which were treated: with doxorubicin alone and incubated for 15 min (a); with the compound obtained in Example 3 and incubated for 15 min (b); and with the compound obtained in Example 3 and incubated for 24 hours (c), respectively. Item (3) shows the fluorescent images of RAW264.7 cells which were treated: with Fl-Arg$_9$ and incubated for 15 min (a); with the compound obtained in Example 5 and incubated for 15 min (b); and with the compound obtained in Example 5 and incubated for 24 hours (c), respectively. Further, Item (4) shows the fluorescent images of RAW264.7 cells which were treated: with Fl-Arg$_9$ and incubated for 15 min (a); with the compound obtained in Example 12 and incubated for 15 min (b); and with the compound obtained in Example 11 and incubated for 15 min (c), respectively. And, item (5) shows the fluorescent images of RAW264.7 cells which were treated: with the compound obtained in Example 13 and incubated for 15 min (b); and with the compound obtained in Example 14 and incubated for 15 min (b), respectively.

As shown in FIG. 1, the inventive molecular transporters conjugated with doxorubicin through a covalent bond display better permeability through a cell membrane than doxorubicin alone or Fl-Arg$_9$.

TEST EXAMPLE 2

Measurement of Transmission Ability into the Mouse Brain

The compounds prepared in Examples 1 (81.8 mg/kg), 3 (95.2 mg/kg, after being conjugated with FITC) and 5 (115.6 mg/kg) were each diluted with distilled water and abdominally injected to 8-week-old C57BL/6 mice (HYO CHANG Science, KR). After 20 min, the injected mice were treated with a euthanasia solution, PBS containing 4% paraformaldehyde (pH 7.4), and the brain of each mouse was harvested and incubated in 0.5 M sucrose PBS solution for 1 day. The brain was sliced into a 15 μm thick slices, and each slice was placed on a slide glass, dried at 37° C., washed with PBS, treated with 0.3% triton X-100 at room temperature for 15 min and observed with a confocal microscope. The results are shown in FIG. 2.

Figure 2:
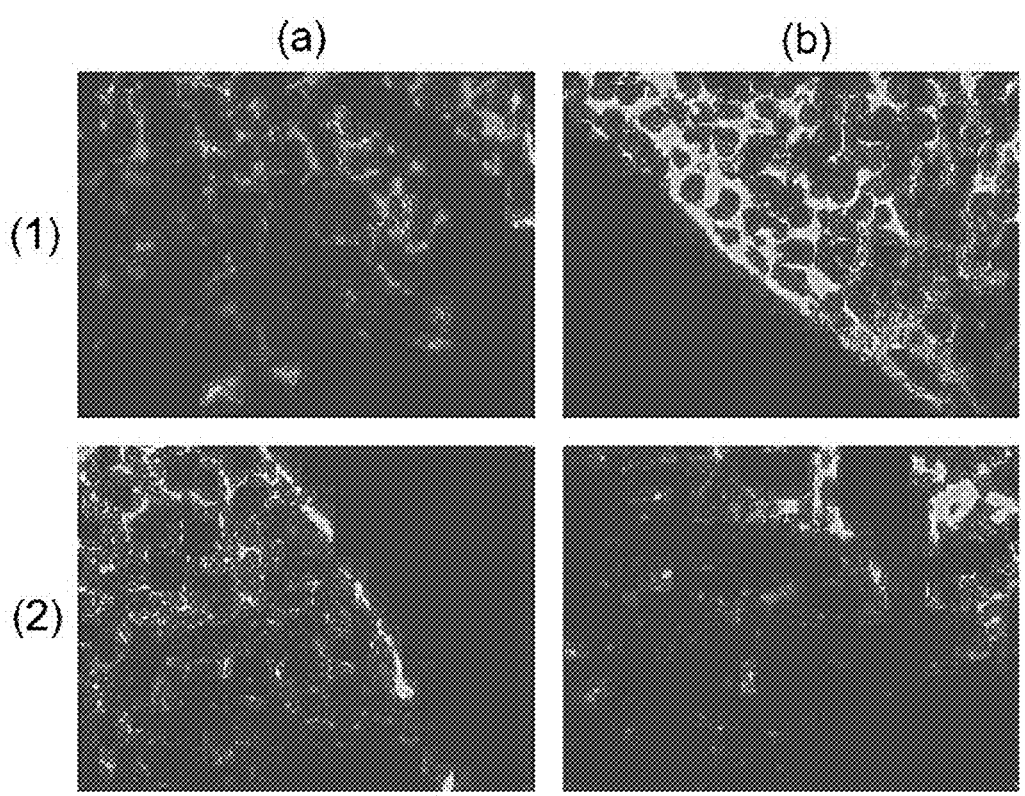
FIG. 2: Results of relative transmission abilities of the molecular transporters through the blood-brain barrier, observed by a confocal microscope.

In FIG. 2, item (1)-(a) shows the result from the mouse injected with only distilled water as a control; and item (1)-(b), the mouse injected with the compound of Example 1. Further, item (2)-(a) shows the result observed for the mouse injected with the compound of Example 5; and item (2)-(b), the mouse injected with the compound of Example 3.

As shown in FIG. 2, the molecular transporters of the present invention can effectively deliver biologically active molecules including paclitaxel or doxorubicin, which by themselves are known to exhibit low blood-brain barrier permeabilities.

While the invention has been described with respect to the above specific embodiments, it should be recognized that various modifications and changes may be made to the invention by those skilled in the art which also fall within the scope of the invention as defined by the appended claims.

What is claimed is:

1. A sugar alcohol of formula 1, or a salt thereof:

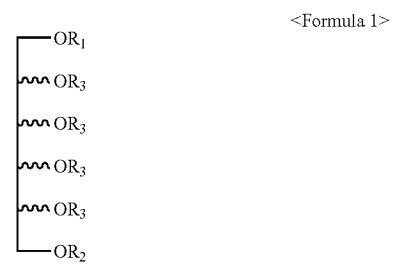

<Formula 1> wherein,

R$_1$ and R$_2$ are each independently H, alkyl, arylalkyl, cycloalkyl, heteroalkyl, —(CH$_2$)$_m$NHR', —(CH$_2$)$_l$CO$_2$R'', —COR''', —SO$_2$R'''', a basic amino acid residue, a fluorescent tag, or a physiologically active molecule selected from the group consisting of doxorubicin and paclitaxel, with the proviso that at least one of R$_1$ and R$_2$ is doxorubicin, paclitaxel, —COR''' or the basic amino acid residue, wherein the basic amino acid is selected from the group consisting of histidine, lysine, and arginine;

R', R'', R''' and R'''' are each independently H, alkyl, arylalkyl, cycloalkyl, heteroalkyl or a physiologically active molecule selected from the group consisting of doxorubicin and paclitaxel;

m is an integer in the range of 2 to 5;

l is an integer in the range of 1 to 5; and

R$_3$ is

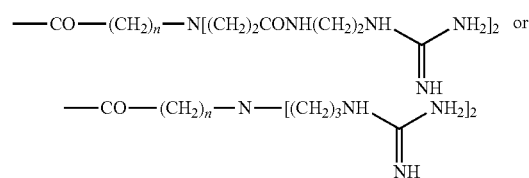

n being an integer in the range of 1 to 12.

2. The sugar alcohol of claim 1, which is an alditol derivative having a skeletal structure of sorbitol, mannitol, galactitol, or a salt thereof.

3. A composition for delivering a biologically active molecule or a nucleic acid across a biological membrane into a cell, wherein the biologically active molecule is doxorubicin or paclitaxel, said composition comprising the compound of Formula 1:

<Formula 1> wherein, $R_1$, $R_2$ and $R_3$ are the same as defined in claim 1, and the biologically active agent or nucleic acid.

4. A method for delivering a biologically active molecule or a nucleic acid across a biological membrane into a cell which comprises the step of employing the compound of formula 1 as a molecular transporter:

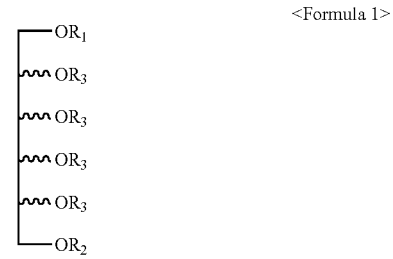

<Formula 1> wherein, $R_1$, $R_2$ and $R_3$ are the same as defined in claim 1, for the delivery of the biologically active active molecule or the nucleic acid.

* * * * *